US008481283B2

(12) United States Patent
O'Leary et al.

(10) Patent No.: US 8,481,283 B2
(45) Date of Patent: Jul. 9, 2013

(54) PRESSURE-ASSISTED MOLECULAR RECOVERY (PAMR) OF BIOMOLECULES, PRESSURE-ASSISTED ANTIGEN RETRIEVAL (PAAR), AND PRESSURE-ASSISTED TISSUE HISTOLOGY (PATH)

(75) Inventors: Timothy J. O'Leary, Washington, DC (US); Jeffrey T. Mason, Rockville, MD (US); Carol B. Fowler, Rockville, MD (US); Robert E. Cunningham, Rockville, MD (US)

(73) Assignees: The United States of America as Represented by the Department of Veterans Affairs, Washington, DC (US); The United States of America as Represented by the Secretary of Defense on behalf of the Armed Forces Institute of Pathology, Washington, DC (US); American Registry of Pathology, Washington, DC (US)

( * ) Notice: Subject to any disclaimer, the term of this patent is extended or adjusted under 35 U.S.C. 154(b) by 0 days.

(21) Appl. No.: 13/613,618

(22) Filed: Sep. 13, 2012

(65) Prior Publication Data
US 2013/0011854 A1 Jan. 10, 2013

Related U.S. Application Data

(62) Division of application No. 12/630,746, filed on Dec. 3, 2009, now Pat. No. 8,288,122.

(60) Provisional application No. 61/119,634, filed on Dec. 3, 2008.

(51) Int. Cl.
*G01N 1/30* (2006.01)

(52) U.S. Cl.
USPC ...................................... 435/40.52; 435/40.5

(58) Field of Classification Search
None
See application file for complete search history.

(56) References Cited

U.S. PATENT DOCUMENTS

| | | | |
|---|---|---|---|
| 6,036,923 | A | 3/2000 | Laugharn, Jr. et al. |
| 6,291,180 | B1 | 9/2001 | Chu |
| 6,569,672 | B1 | 5/2003 | Laugharn, Jr. et al. |
| 6,610,488 | B2 | 8/2003 | Danenberg et al. |
| 6,635,469 | B1 | 10/2003 | Litt et al. |
| 6,995,020 | B2 | 2/2006 | Capodieci et al. |
| 2001/0051365 | A1 * | 12/2001 | Morales et al. ............ 435/173.4 |
| 2004/0029184 | A1 | 2/2004 | Gourevitch |
| 2004/0038333 | A1 | 2/2004 | Randolph et al. |
| 2005/0019814 | A1 | 1/2005 | Laugharn et al. |
| 2005/0136122 | A1 | 6/2005 | Sadozai et al. |
| 2008/0153127 | A1 | 6/2008 | Morales et al. |
| 2009/0124510 | A1 | 5/2009 | Porschewski et al. |

FOREIGN PATENT DOCUMENTS
JP 2001-521818 11/2001

OTHER PUBLICATIONS

Fowler et al., "Tissue surrogates'as a model for archival formalin-fixed paraffin-embedded tissues," *Laboratory Investigation*, vol. 87, pp. 836-846, 2007.
Fowler et al., "Elevated hydrostatic pressure promotes protein recovery from formalin-fixed, paraffin-embedded tissue surrogates," *Laboratory Investigation*, vol. 88, pp. 185-195, 2008.
Fowler et al., "Modeling formalin fixation and histological processing with ribonuclease A: effects of ethanol dehydration on reversal of formaldehyde cross-links," *Laboratory Investigation*, vol. 88, pp. 785-791, 2008.
Guo et al., "Proteome Analysis of Microdissected Formalin-fixed and Paraffin-embedded Tissue Specimens," *Journal of Histochemistry & Cytochemistry*, vol. 55, No. 7, pp. 763-772, 2007.
Pileri et al., "Antigen Retrieval Techniques in Immunohistochemistry: Comparison of Different Methods," *Journal of Pathology*, vol. 183, pp. 116-123, 1997.
Rait et al., "Modeling formalin fixation and antigen retrieval with bovine pancreatic ribonuclease A: I—Structural and functional alterations," *Laboratory Investigation*, vol. 84, pp. 292-299, 2004.
Rait et al., "Modeling formalin fixation and antigen retrieval with bovine pancreatic RNase A II. Interrelationship of cross-linking, immunoreactivity, and heat treatment," *Laboratory Investigation*, vol. 84, pp. 300-306, 2004.
Rait et al., "Conversions of Formaldehyde-modified 2'-Deoxyadenosine 5'-Monophosphate in Conditions Modeling Formalin-fixed Tissue Dehydration," *Journal of Histochemistry & Cytochemistry*, vol. 54, No. 3, pp. 301-310, 2006.
Shi et al., "A Technique for Retrieving Antigens in Formalin-fixed, Routinely Acid-decalcified, Celloidin-embedded Human Temporal Bone Sections for Immunohistochemistry," *Journal of Histochemistry & Cytochemistry*, vol. 40, No. 6, pp. 787-792, 1992.
Shi et al., "Antigen Retrieval Immunohistochemistry Under the Influence of pH using Monoclonal Antibodies," *Journal of Histochemistry & Cytochemistry*, vol. 43, No. 2, pp. 193-201, 1995.
Shi et al., "Antigen Retrieval Immunohistochemistry: Past, Present, and Future," *Journal of Histochemistry & Cytochemistry*, vol. 45, No. 3, pp. 327-343, 1997.
Yamashita et al., "Mechanisms of Heat-Induced Antigen Retrieval: Analyses in Vitro Employing SDS-PAGE and Immunohistochemistry," *Journal of Histochemistry and Cytochemistry*, vol. 53, No. 1, pp. 13-21, 2005.

* cited by examiner

*Primary Examiner* — Allison Ford
*Assistant Examiner* — Yvonne Pyla
(74) *Attorney, Agent, or Firm* — Klarquist Sparkman, LLP

(57) ABSTRACT

A method is disclosed for reversing fixation-induced cross-linking in tissue specimens that have been preserved for histological examination. The method involves placing the fixed tissue in a liquid under elevated temperature and pressure conditions that are sufficient to reverse the fixation-induced cross-linking, restore antigenicity to proteins, and permit improved molecular and proteomic analysis of the preserved tissue specimen. Methods are also disclosed for processing tissues for histological examination under elevated pressure conditions that enhance the perfusion of liquid reagents into the tissue and reduce overall processing times.

16 Claims, 17 Drawing Sheets

SEQUENCE LISTING

<160> NUMBER OF SEQ ID NOS: 2

<210> SEQ ID NO 1
<211> LENGTH: 129
<212> TYPE: PRT
<213> ORGANISM: Gallus gallus

```
                        -continued

<400> SEQUENCE: 1

Lys Val Phe Gly Arg Cys Glu Leu Ala Ala Ala Met Lys Arg His Gly
1               5                   10                  15

Leu Asp Asn Tyr Arg Gly Tyr Ser Leu Gly Asn Trp Val Cys Ala Ala
            20                  25                  30

Lys Phe Glu Ser Asn Phe Asn Thr Gln Ala Thr Asn Arg Asn Thr Asp
        35                  40                  45

Gly Ser Thr Asp Tyr Gly Ile Leu Gln Ile Asn Ser Arg Trp Trp Cys
    50                  55                  60

Asn Asp Gly Arg Thr Pro Gly Ser Arg Asn Leu Cys Asn Ile Pro Cys
65                  70                  75                  80

Ser Ala Leu Leu Ser Ser Asp Ile Thr Ala Ser Val Asn Cys Ala Lys
                85                  90                  95

Lys Ile Val Ser Asp Gly Asn Gly Met Asn Ala Trp Val Ala Trp Arg
            100                 105                 110

Asn Arg Cys Lys Gly Thr Asp Val Gln Ala Trp Ile Arg Gly Cys Arg
        115                 120                 125

Leu

<210> SEQ ID NO 2
<211> LENGTH: 147
<212> TYPE: PRT
<213> ORGANISM: Gallus gallus

<400> SEQUENCE: 2

Met Arg Ser Leu Leu Ile Leu Val Leu Cys Phe Leu Pro Leu Ala Ala
1               5                   10                  15

Leu Gly Lys Val Phe Gly Arg Cys Glu Leu Ala Ala Ala Met Lys Arg
            20                  25                  30

His Gly Leu Asp Asn Tyr Arg Gly Tyr Ser Leu Gly Asn Trp Val Cys
        35                  40                  45

Ala Ala Lys Phe Glu Ser Asn Phe Asn Thr Gln Ala Thr Asn Arg Asn
    50                  55                  60

Thr Asp Gly Ser Thr Asp Tyr Gly Ile Leu Gln Ile Asn Ser Arg Trp
65                  70                  75                  80

Trp Cys Asn Asp Gly Arg Thr Pro Gly Ser Arg Asn Leu Cys Asn Ile
                85                  90                  95

Pro Cys Ser Ala Leu Leu Ser Ser Asp Ile Thr Ala Ser Val Asn Cys
            100                 105                 110

Ala Lys Lys Ile Val Ser Asp Gly Asn Gly Met Asn Ala Trp Val Ala
        115                 120                 125

Trp Arg Asn Arg Cys Lys Gly Thr Asp Val Gln Ala Trp Ile Arg Gly
    130                 135                 140

Cys Arg Leu
145
```

PRESSURE-ASSISTED MOLECULAR RECOVERY (PAMR) OF BIOMOLECULES, PRESSURE-ASSISTED ANTIGEN RETRIEVAL (PAAR), AND PRESSURE-ASSISTED TISSUE HISTOLOGY (PATH)

CROSS REFERENCE TO RELATED APPLICATION

This is a divisional of U.S. patent application Ser. No. 12/630,746, filed Dec. 3, 2009, now U.S. Pat. No. 8,288,122 which claims the benefit of U.S. Provisional Application No. 61/119,634, filed Dec. 3, 2008, both of which are incorporated herein in their entirety.

ACKNOWLEDGMENT OF GOVERNMENT SUPPORT

This invention was made with government support under grant number 5R33CA107844-03 awarded by the Department of Health and Human Services. The government has certain rights in the invention.

FIELD

Methods are disclosed to reverse chemical cross-links and adducts induced by cross-linking fixatives, such as formaldehyde, so that biological molecules can be more reliably isolated from, or identified in, fixed tissue specimens. The biological molecules may be proteins or nucleic acids isolated for use in proteomic or genomic studies. This method can also be used to identify antigens and enzymes in fixed tissue specimens that are subjected to immunohistochemical or enzyme histochemical studies. Reversal of fixation-induced cross-linking permits patterns of gene expression and chromosomal alterations to be reliably determined in archived tissue samples, for example when performing proteomic studies related to development and progression of diseases such as cancer.

BACKGROUND

The molecular pathogenesis of cancer and other diseases is related to genetic changes, such as mutation or altered gene expression. For example, genetic changes in tumors can be correlated to cancer metastasis, treatment outcome, and survival using modern high-throughput molecular biologic and proteomic methods. This biological information permits the development and selection of therapeutic agents targeted to specific molecular alterations in the tumor. When the clinical course is short, as in pancreatic cancer, the molecular information can be obtained using fresh or frozen tissue from which intact mRNA and protein is easily extracted. However, for cancers that have a longer clinical course (such as breast and prostate cancer) many years may elapse between initial diagnosis or treatment and the appearance of metastases. In these instances, clinical correlations are obtained using formalin-fixed paraffin-embedded (FFPE) tissues. Unfortunately, analysis of rare mRNA transcripts by RT-PCR from FFPE tissue is currently unreliable. Large-scale multiplex techniques (such as proteomic analysis, serial analysis of gene expression, and gene chip methods) using FFPE tissue have therefore been unreliable.

Most archival tissues have been "fixed" by soaking them in a solution of 3.7% (w/v) formaldehyde, dehydrating them through a series of water/alcohol solutions and xylene, and then embedding them in paraffin wax. This procedure facilitates morphologic examination by preserving cellular integrity. The major method by which formaldehyde achieves this goal is by inactivation of nucleases, proteases, lipases, and saccharidases that cause cells and tissues to "self-destruct" after death or excision.

Attempts have been made to develop fixatives that better preserve tissue for genomic and proteomic analysis, but they are not widely used. Thus, most tissue archives consist of specimens that have been fixed with formaldehyde, dehydrated, and embedded in paraffin wax. Although formaldehyde reaction chemistry has been widely investigated, little attention has been given to studying the processes of dehydration and paraffin embedding that follow fixation, but precede microscopic examination. The understanding of the chemical processes that occur when tissue is prepared for microscopic examination is thus incomplete, which has frustrated the development of methods by which this process could be sufficiently reversed to yield macromolecules suitable for molecular analysis, such as proteomic analysis.

Formaldehyde fixes proteins in tissue by cross-linking basic amino acids, such as lysine and glutamine, and through the formation of methylol adducts with these basic amino acids. Both intra-molecular and inter-molecular cross-links are formed. These cross-links preserve protein secondary structure while destroying enzyme activity by forming active-site adducts, which prevent enzyme conformational changes and inhibit diffusion of both enzyme and substrate through the cellular matrix. Formaldehyde reacts with uncharged amino groups (such as the ε-amino group of Lys) to form highly reactive methylol compounds by the reaction:

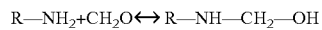

Under suitable steric conditions, the reactive methylol compounds condense with amide, phenol, indole, and imidazole side chains to form methylene bridges that cross-link polypeptide chains by reactions such as:

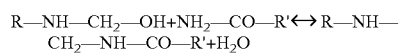

These reactions have discouraged investigators from using FFPE archival tissues for proteomic analysis. Two-dimensional (2-D) gel electrophoresis requires that protein molecules not "stick" to each other, because they must be solubilized to be loaded on the gel and separated by molecular weight during electrophoresis. Furthermore, 2-D separation requires protein ionization for successful isoelectric focusing. The formation of either methylol adducts or methylene cross-links neutralizes basic amines, which significantly perturbs the isoelectric focusing step.

Another unwanted effect of formaldehyde fixation is a reduction of immunohistochemical reactivity in tissue sections. This loss of reactivity is believed to arise from chemical epitope modification and the inability of antibodies to diffuse into the cross-linked tissue. These effects may be partially reversed by exposure of fixed tissue sections to high temperatures for short periods of time in the presence of aqueous salt or protein denaturant solutions. Shi et al. (*J. Histochem. Cytochem.* 39:741-748, 1991) have demonstrated that heat treatment can improve retrieval of antigens masked by formalin fixation and that optimal results are correlated with the product of the heating temperature and the time of heat treatment (*CAP Today* 9:116-123, 1995).

The pH of the antigen retrieval (AR) solution has also been found to play a role in staining patterns of fixed tissue. Three distinct staining patterns have been identified: (a) optimal staining at low and high pH; (b) optimal staining correlated with increasing pH; and (c) optimal staining independent of pH (Shi et al., *J. Histochem. Cytochem.* 43:193-201, 1995). A variety of salt and protein denaturant solutions have been employed for AR; however, no single chemical component has been shown to be universally required or optimal for antigen unmasking (Shi et al., *J. Histochem. Cytochem.* 45:327-343, 1997).

Shi et al. (*J. Histochem. Cytochem.* 40:787-792, 1992) have also proposed that the unwanted modification of protein structure by formalin is reversed by treatment with an antigen retrieval (AR) buffer at room temperature.

Processing tissue for histological examination is time consuming, often requiring up to 24 hours to complete. This processing period delays the examination of tissue biopsies by pathologists. In the case of surgical pathology, a surgeon may be waiting for a diagnosis to decide how to proceed, and this delay is costly and can cause harm to the patient. To avoid this problem, rapidly prepared frozen tissue sections are used in surgical pathology, however, such tissue sections lack the anatomic detail of conventional FFPE tissue sections.

Others have recognized the need to shorten the time required for tissue processing, but they have made only modest improvements in the conventional methods. To accelerate tissue processing, U.S. Pat. Nos. 4,656,047, 4,839,194, and 5,244,787 use microwave energy; U.S. Pat. Nos. 3,961,097 and 5,089,288 use ultrasonic energy; and U.S. Pat. No. 5,023,187 uses infrared energy. U.S. Patent Publication 2008/0153127 discloses a method of rapid fixation of tissue specimens at a temperature of 30-65° C. under sub-atmospheric pressure.

SUMMARY OF THE DISCLOSURE

Although formaldehyde adducts and cross-linkages associated with proteins and nucleic acid bases are reversed in water, subsequent exposure to ethanol (the second step in tissue fixation) drastically reduces the ability to reverse these formaldehyde modifications (Fowler et al., *Laboratory Investigation* 87:836-846, 2007, incorporated herein in its entirety). Exposure to ethanol leads to dehydration of biological molecules and their subsequent aggregation through hydrophobic contacts (Rait et. al, *J. Histochem Cytochem.* 54:301-310, 2006). In the aggregated state, unreacted methylol adducts can lead to additional intermolecular cross-linking. The inventors have determined that a major impediment to formaldehyde adduct reversal in FFPE tissue is the re-hydration of these highly cross-linked molecular aggregates. Incubation of FFPE tissue at high temperatures can facilitate this re-hydration, but at the expense of thermally-induced molecular degradation.

The methods disclosed herein address this problem by exposing deparaffinized fixed tissue specimens to elevated temperature and pressure, but using lower elevated temperatures than would otherwise be required to induce the hydration of the cross-linked molecular aggregates that result from tissue fixation. In some examples, the method includes hydrating a fixed tissue specimen in a liquid, applying elevated temperature and pressure for a sufficient period of time to reverse at least a portion of cross-links in the tissue specimen, wherein the pressure is at least 1000 psi and recovering biological molecules for further purification and/or characterization. In particular examples, the pressure is at least 1000 psi (for example, at least 5000 psi, or at least 10,000 psi, such as 10,000-100,000 psi), the temperature is about 60-100° C. (for example, about 60° C., 80° C., or 100° C.) and the time is at least about 15 minutes (such as at least 30 minutes, at least 1 hour, at least 2 hours, for example, about 15 minutes to 24 hours). This method results in the reversal of formaldehyde adducts and cross-linkages in biological molecules without the deleterious effects of high temperature treatment. This method in turn facilitates the use of FFPE tissue in proteomics, genomics, glycomics, and clinical pathology. The method also helps restore the antigenicity of antigen targets in the tissue specimen.

The rate-limiting step in tissue histology processing is the slow perfusion of solvents into the tissues. This is particularly true for the initial fixation step, which most commonly involves formaldehyde cross-linking.

A method is therefore also disclosed that uses elevated hydrostatic pressure to increase the rate of perfusion of solvent into tissues during processing of tissue for histological examination. In some examples, the method includes placing tissue in a tissue fixative under elevated pressure for a sufficient period of time to increase the perfusion of the fixative into the tissue, dehydrating the tissue by exposing to a sequential series of dehydrating solvents under the elevated pressure, and perfusing embedding medium into the tissue under the elevated pressure. In particular examples, the elevated pressure is at least 1000 psi (for example, at least 5000 psi, or at least 10,000 psi, such as 10,000-100,000 psi). In further examples, the temperature is about 24-100° C. (for example, about 60° C., 80° C., or 100° C.) and the elevated pressure and temperature is maintained for at least about 15 minutes (such as at least 1 hour, at least 2 hours, for example, about 15 minutes to 5 hours). In additional embodiments, the elevated pressure is applied for two or more cycles, where one cycle is a period of time at elevated pressure (for example, at least about 30 seconds, about 60 seconds, about 90 seconds, about 2 minutes or more) followed by a period of time at ambient pressure (such as at least about 15 seconds, about 20 seconds, about 25 seconds, about 30 seconds, about 40 seconds, about 50 seconds, about 60 seconds, or more). Rapid solvent perfusion permits rapid tissue histological examination without the deleterious effects caused by the use of ultrasonic radiation or the examination of fresh-frozen tissue.

BRIEF DESCRIPTION OF DRAWINGS

FIG. 1A shows a piston screw pump, pressure gauge, suspension liquid reservoir, and liquid inlet and shut-off valve. FIG. 1B shows a cylindrical specimen cylinder with end caps (3 mm id×30 mm length), a temperature collar surrounding the specimen cylinder, and an electronic temperature controller capable of heating the tissue suspension at temperatures from 24 to 120° C.

SEQUENCE LISTING

Figure 1:
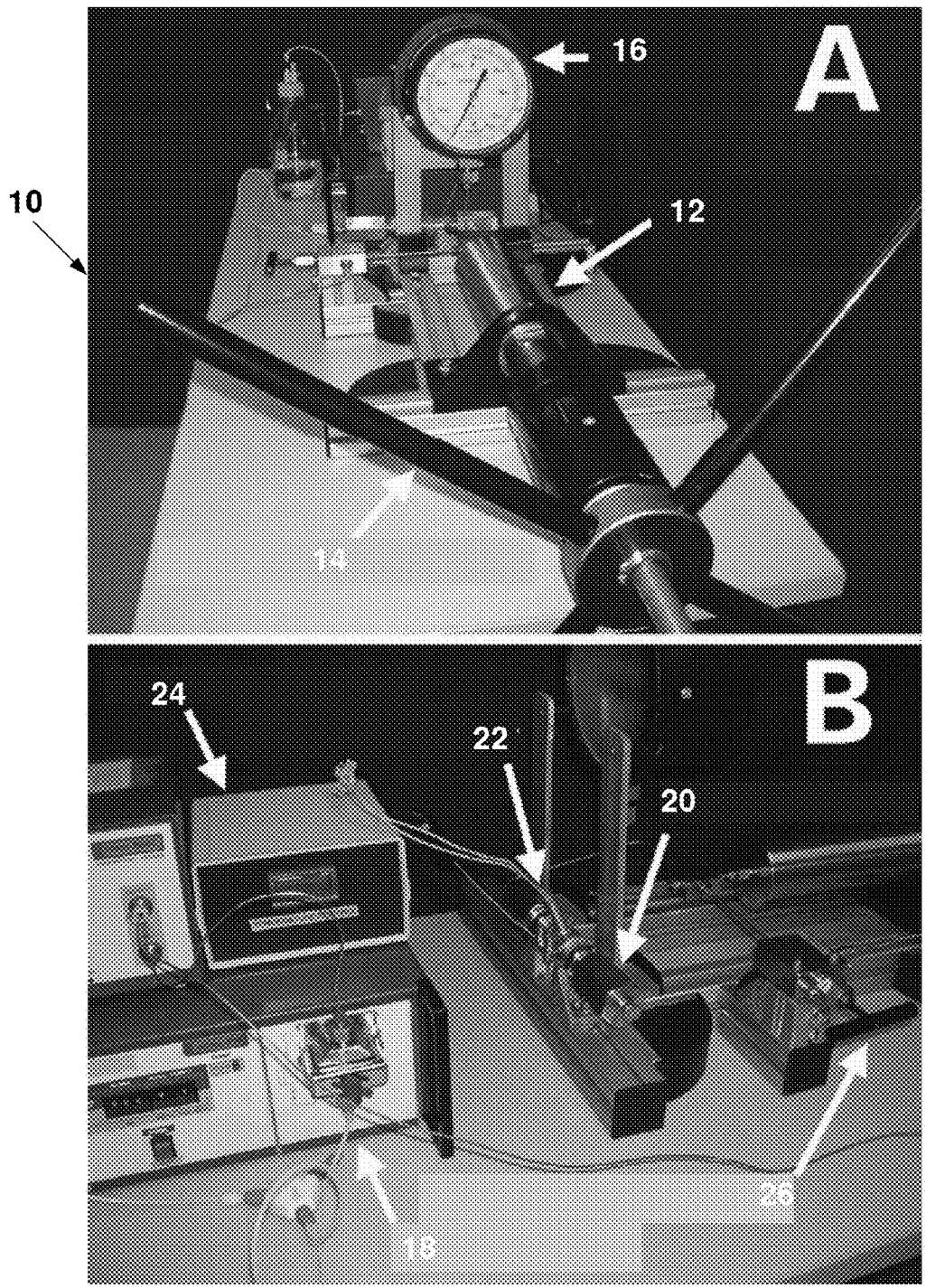
FIG. 1 is a digital image of a pressure apparatus suitable for pressure-assisted molecular recovery (PAMR). The device is a high-pressure generator that uses a manually operated piston screw pump to compress a liquid in a small-bore cylinder to generate pressures up to 75,000 psi.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

The Sequence Listing is submitted as an ASCII text file in the form of the file named Sequence_Listing.txt, which was created on Sep. 11, 2012, and is 3,268 bytes, which is incorporated by reference herein. In the accompanying sequence listing:

SEQ ID NOs: 1 and 2 are the amino acid sequences of hen egg white lysozyme from mass spectrometric analysis of a lysozyme tissue surrogate.

DETAILED DESCRIPTION

Described herein is a method for pressure-assisted molecular recovery (PAMR) of biological molecules that have been "fixed" in various media. As indicated previously, a biological molecule is fixed in a medium through the formation of adducts with molecules, such as formaldehyde, present in the medium and subsequent cross-link formation between the adducted molecules and other biomolecules present in the specimen.

ABBREVIATIONS

AR: antigen retrieval
DTPA: diethylenetriaminepentaacetic acid
EDTA: ethylenediaminetetraacetic acid
FFPE: formalin-fixed paraffin embedded
PAAR: pressure-assisted antigen retrieval
PAMR: pressure-assisted molecular recovery
PATH: pressure-assisted tissue histology
SDS: sodium dodecyl sulfate
TMAO: trimethylamine-N-oxide
TRIS: tris(hydroxymethyl)aminomethane

TERMS

"Biological molecules" include soluble proteins, membrane-associated proteins, glycoproteins, ribonucleic acid, deoxyribonucleic acid, antibodies, lipids, carbohydrates, and molecules originating from pathogens.

"Buffering compounds" include acetate, phosphate, PBS (phosphate-buffered-saline), citrate, borate, carbonatebicarbonate, Tris [Tris(hydroxymethyl)amino methane], Tris-acetate-EDTA (ethylenediaminetetraacetic acid), Tris-borate, Tris-glycine, HEPES [4-(2-hydroxyethyl)piperazine-1-ethanesulfonic acid], MES [2-(N-morpholino)ethansulfonic acid], TAPS [N-tris(hydroxymethyl)-3-aminopropane sulfonic acid], and MOPS [3-(N-morpholino) propanesulfonic acid]. An "antigen retrieval (AR) buffer" is a solution that includes a buffer and which is used in retrieval of an antigen from a substrate, such as a tissue specimen. Antigen retrieval buffers are reviewed in Kim et al., *Journal of Molecular Histology* 35:409-416, 2004.

"Chelators" include EDTA, potassium oxalate, calcein, DDAO [N,N-dimethyldecylamino-N-oxide], and DTPA [diethylenetriaminepentaacetic acid].

"Chemical additives" include chelators, formaldehyde and Schiffs base scavengers, denaturing agents, detergents, oxidizing or reducing agents, osmolytes, and enzymes or enzyme inhibitors.

"Cross-linking agents" include formaldehyde, paraformaldehyde, glutaraldehyde, and 1-ethyl-3-(3-dimethylaminopropyl).

"Denaturing agents" include urea, guanidine hydrochloride, glycerol, and SDS [sodium dodecyl sulfate].

"Detergents" include SDS, TRITON® X-100 detergent, TWEEN® 20 detergent, ASB [3-(N,N-dimethyl(3-myristoylaminopropyl)amino)propane sulfonate], Brj-56 [polyethylene glycol hexadecyl ether], C7BzO [3-(4-heptyl)phenyl-3-hydroxypropyl)dimethylammonium propanesulfonate], octyl-13-D-glucopyranoside, CHAPS [3-(3-cholamidopropyl)-dimethylammonio)-1-propanesulfonate], polyoxyethylene 10 tridecyl ether, N-dodecyl-(3-D-maltoside, octyl-(3-D-thioglucopyranoside, and 3-(decyldimethylammonio) propanesulfonate inner salt.

"Elevated pressure" is a pressure above atmospheric pressure, and in specific examples described herein includes pressures between 1000 psi and 75,000 or 100,000 psi, between 25000 psi and 75,000 psi, and between 5000 psi and 50,000 psi.

Elevated pressure may be generated in a closed vessel using a pumping system (an air or inert gas hydraulic process), or a high-pressure generator (a manually operated piston screw pump). The pressure of pumping systems or high-pressure generators can be increased using gas boosters or hydraulic intensifiers. Manufacturers of complete high-pressure systems and individual system components include Pressure BioSciences, Inc. (South Easton, Mass.), High-Pressure Equipment Company (Erie, Pa., U.S.A.), and AppliTech Corporation (Lancaster, Pa., U.S.A.).

"Elevated temperatures" are temperatures above normal room temperature (about 24° C.) and in specific examples disclosed herein include temperatures between 24° C. and 120° C., between 24° C. and 80° C., and between 24° C. and 60° C. In specific examples disclosed herein, the elevated temperatures are 50, 60, 65, 70, 80, 90, 95, or 100° C.

Elevated pressures and/or temperatures may be applied for any time period that is capable of reversing a portion of the cross-links formed by a cross-linking agent. In some embodiments, substantially all of the cross-links are reversed. Examples of time periods include between 15 minutes and 24 hours, between 15 minutes and 3 hours, between 15 minutes and 2 hours, and between 15 minutes and 60 minutes.

"Enzymes" are biomolecules that catalyze chemical reactions, and they include proteases, peptidases, nucleases, glycosylases, lipases, and phosphatases.

"Enzyme inhibitors" include biological or synthetic inhibitors of enzymes, such as the individual aforementioned enzymes. The choice of enzyme or enzyme inhibitor will depend upon the target biological molecule whose activity is to be recovered.

"Fixation" refers to the process by which a tissue specimen is preserved as a fixed specimen, for example by placing the tissue specimen in a fixative (such as formaldehyde), and dehydrating the tissue (for example by exposure to an alcohol). Fixed tissues are then often embedded in a preservation medium (such as paraffin) for long-term storage.

"Formaldehyde and Schiff's base scavengers" include 5'-deoxypyridoxal, pyridoxyl 5'-phosphate, pyridoxalamine, glycine, trimethylamine, citraconic anhydride, dimedone, aminoguanidine, cysteine, N-acetyl cysteine, resorcinol, bisulfites, and sulfites.

"Hydrating" a tissue specimen refers to introducing water into it, for example by placing the specimen in a liquid that contains water, such as an alcohol/water liquid or in water alone.

"Liquid" includes water, alcohols, aprotic solvents, protic solvents, organic acids, organic bases, and supercritical fluids, water-alcohol mixtures, solutions containing a buffering compound and additional chemical additives.

"Media" are substances in which tissue can be placed for examination, and these substances include paraffin, paraffin-containing compounds, araldite, celloidin, DURCUPAN™ embedding medium, epoxy, glycol methacrylate, hydroxypropyl methacrylate, JB-4™ embedding medium, Spurr, and LR WHITE™ embedding medium.

"Osmolytes" include glycerol, sucrose, trehalose, L-arginine, L-proline, betaine, TMAO [trimethylamine-N-oxide], urea, taurine, cyclodextrin, polyvinylpyrrolidone, polyethylene glycol, gamma-aminobutyric acid, GroEL, DnaK, L-serine, sarcosine, and osmolytes from hyper-thermophilic organisms.

"Oxidizing and reducing agents" include 2-mercaptoethanol, dithiothreitol, 2-mercaptoethylamine hydrochloride, TCEP [tris(2-carboxyethyl)phosphine], copper, L-arginine, triethyloxonium fluoroborate, acetamide, and glutathione.

The pH of solutions disclosed herein for treating tissue specimens are suitable pHs for processing, and in disclosed examples may be between 2 and 12, between 4 and 9, between 5 and 8, or around 7.

"Substrate" includes glass, plastic, metal, and nitrocellulose.

"Tissue" includes whole organs, organ sub-structures, surgical tissue biopsies, punch biopsies, fine-needle aspirate biopsies, bone, biological fluids, archival tissues. "Tissue samples" are specimens of the tissue that have been taken for evaluation, such as tissue sections mounted on a substrate (such as a glass slide).

As used herein and in the appended claims, the singular forms "a," "an," and "the" include plural referents unless the context clearly dictates otherwise. Thus, for example, reference to "a genetic alteration" includes a plurality of such alterations and reference to "a tissue specimen" includes reference to one or more tissue specimens, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All patents and publications mentioned herein are incorporated herein by reference in their entirety.

Publications cited herein are cited for their disclosure prior to the filing date of the present application. Nothing here is to be construed as an admission that the inventors are not entitled to antedate the publications by virtue of an earlier priority date, prior date of invention, or demonstrating that the disclosed work is the inventors' own work. Further the actual publication dates may be different from those cited and require independent verification.

Pressure-Assisted Molecular Recovery (PAMR)

One embodiment of the disclosed method is a pressure-assisted molecular recovery (PAMR) method for recovering biological molecules from a tissue specimen fixed with a cross-linking agent. The method includes hydrating the fixed tissue specimen in a liquid, applying elevated temperature and pressure to the liquid for a sufficient period of time to reverse cross-links formed by the cross-linking agent, and recovering the biological molecules for further purification and/or characterization. Hydration of the tissue can take place by suspending the fixed tissue specimen in a liquid solution, for example by homogenizing the tissue and suspending the homogenate of the fixed tissue specimen in the liquid solution. In particular examples, the elevated pressure is at least 1000 psi, at least 2500 psi, at least 5000 psi, at least 10,000 psi, at least 15,000 psi, at least 40,000 psi, or is in the range of about 2500-100,000 psi, such as about 25000-75,000 psi, about 5000-50,000 psi, or about 40,000-45,000 psi. In certain examples, the pressure is also less than 100,000 psi or 75,000 psi.

The elevated temperature at which the liquid is subjected to elevated pressure is a controlled temperature of at least 50° C. (such as at least 55° C., at least 60° C., at least 65° C., at least 75° C., or at least 80° C.), for example, 50-120° C. or 65-100° C., such as a temperature of about 80° C. for about 2 hours, or a temperature of about 100° C. for about 2 hours. In certain examples, the elevated temperature is also less than about 100° C. In particular examples, the elevated temperature is at or above the temperature at which one or more proteins in the sample become denatured. The temperature at which a protein becomes denatured depends on multiple factors, including pI of the protein, pH of the solution and the presence of additional agents in the solution, for example, detergent and/or denaturing agents. One of skill in the art can determine the temperature at which a particular protein will become denatured in a particular solution.

In some examples, the liquid is maintained at a pH of at least about 2 (such as at least 2, at least 4, at least 6, at least 7, or at least 9), for example a pH of about 2-12, 4-9, or 4-6. In certain examples, the pH is also less than about 12 or 9 or 6. In certain examples, the pH is about 2, about 4, about 7, or about 9 (+/−0.5).

The method is suitable to recover from fixed specimens a variety of biological molecules, such as soluble proteins, membrane-associated proteins, glycoproteins, ribonucleic acid, deoxyribonucleic acid, antibodies, lipids, carbohydrates, or molecules originating from pathogens. The biological molecules may be contained in, or recovered from, fixed specimens of whole organs, organ substructures, surgical tissue biopsies, punch biopsies, fine-needle aspirate biopsies, bone, biological fluids, archival tissues, frozen tissue, or tissue sections mounted on a substrate, such as a glass slide. The tissue specimen in some instances has been embedded in media such as paraffin, paraffin-containing compounds, araldite, celloidin, DURCUPAN™ embedding medium, epoxy, glycol methacrylate, hydroxypropyl methacrylate, JB-4™ embedding medium, Spurr, or LR WHITE™ embedding medium. The fixed specimens have been fixed with a variety of cross-linking agents, such as formaldehyde, paraformaldehyde, glutaraldehyde, or 1-ethyl-3-(3-dimethylaminopropyl).

The liquid solution in which the tissue is hydrated can be a solution that includes water, alcohols, organic solvents, aprotic solvents, protic solvents, organic acids, organic bases, or supercritical fluids. In particular examples, the liquid includes water or water-alcohol with a buffering agent, and optional chemical additives. Examples of suitable buffering agents include acetate, phosphate, PBS (phosphate-buffered-saline), citrate, borate, carbonate-bicarbonate, Tris [Tris(hydroxymethyl)amino methane], Tris-acetate-EDTA (ethylenediaminetetraacetic acid), Tris-borate, Tris-glycine, HEPES [4-(2-hydroxyethyl)piperazine-1-ethanesulfonic acid], MES [2-(N-morpholino)ethansulfonic acid], TAPS [N-tris(hydroxymethyl)-3-aminopropane sulfonic acid], or MOPS [3-(N-morpholino)propanesulfonic acid].

Examples of chemical additives that may be added to the liquid include chelators, formaldehyde and Schiff's base scavengers, denaturing agents, detergents, oxidizing or reducing agents, osmolytes, enzymes or enzyme inhibitors. Suitable chelators include EDTA, potassium oxalate, calcein, DDAO [N,N-dimethyldecylamino-N-oxide], or DTPA [diethylenetriaminepentaacetic acid]. Examples of formaldehyde and/or Schiff's base scavengers include 5'-deoxypyridoxal, pyridoxyl 5'-phosphate, pyridoxalamine, glycine, trimethylamine, citraconic anhydride, dimedone, aminoguanidine, cysteine, N-acetyl cysteine, resorcinol, bisulfites, and sulfites. Examples of suitable denaturing agents include urea, guanidine hydrochloride, glycerol, and SDS [sodium dodecyl sulfate]. Examples of suitable detergents include SDS [sodium dodecyl sulfate], TRITON® X-100 detergent, TWEEN® 20 detergent, ASB [3-(N,N-dimethyl(3-myristoylaminopropyl)amino)propane sulfonate], Brij-56 [polyethylene glycol hexadecyl ether], C7BzO [3-(4-heptyl)phenyl-3-hydroxypropyl)dimethylammonium propanesulfonate], octyl-β-D-glucopyranoside, CHAPS [3-(3-chola-midopropyl)-dimethylammonio)-1-propanesulfonate], polyoxyethylene 10 tridecyl ether, N-dodecyl-β-D-maltoside, octyl-β-D-thioglucopyranoside, and 3-(decyldimethylammonio)propanesulfonate inner salt. Examples of suitable oxidizing or reducing agents are 2-mercaptoethanol, dithiothreitol, 2-mercaptoethylamine hydrochloride, TCEP [tris(2-carboxyethyl)phosphine], copper, L-arginine, triethyloxonium fluoroborate, acetamide, and glutathione. Examples of osmolytes include glycerol, sucrose, trehalose, L-arginine, L-proline, betaine, TMAO [trimethylamine-N-oxide], urea, taurine, cyclodextrin, polyvinylpyrrolidone, polyethylene glycol, gamma-aminobutyric acid, GroEL, DnaK, L-serine, sarcosine, and osmolytes from hyper-thermophilic organisms. Examples of suitable enzyme additives include proteases, peptidases, nucleases, glycosylases, lipases, and phosphatases, and examples of the enzyme inhibitors are biological or synthetic inhibitors of the individual aforementioned enzymes.

In some examples, the chemical additive includes agents that promote protein hydrolysis (such as hydrolysis at aspartyl residues). In one example, protein hydrolysis is increased by chemical means, for example by addition of cyanogen bromide, formic acid, or thiotrifluoroacetic acid to the liquid. In a particular example, about 0.01 to 5 g/ml CNBr (for example, about 0.1 to 2 g/ml, or about 0.5 to 1 g/ml) is added to the liquid.

In other examples, protein hydrolysis is increased using biological agents such as proteolytic enzymes, catalytic nucleic acids, or catalytic antibodies. In some examples, proteolytic enzymes, such as one or more proteolytic enzyme that is active at the temperatures utilized in the methods provided herein (for example, about 50° C. to about 100° C.) is added to the liquid. For example, heat-stable proteolytic enzymes are known to one of skill in the art, such as thermolysin protease from *Bacillus thermoproteolyticus rokko* and Protease S from *Pyrococcus furiosus*. Of particular use are heat-stable proteolytic enzymes isolated from thermophilic microorganisms capable of growing at or above 80° C.-100° C., such as thermophilic archaea and bacteria. Examples of thermophilic microorganisms from which heat-stable proteolytic enzymes can be isolated are *Thermus aquaticus, Pyrococcus furiosus, Sulfolobus acidocaldarius, Thermococcus stetteri,* and *Pyrobaculum aerophilum. Pyrococcus furiosus, Aquifex aeolicus, Thermus thermophilus, Thermotoga maritima, T. neapolitana, Bacillus stearothermophilus, Crenarchaeota, Sulfolobus shibatae, S. solfataricus b, S. islandicus, Stygiolobus azoricus, Acidianus infernus, A. ambivalens, Thermoproteus tenax, T. neutrophilus, T. uzoniensis, Pyrobaculum islandicum, P. organotrophum, P. aerophilum b,* *Thermofilum pendens, Desulfurococcus mobilis, D. amylolyticus, Staphylothermus marinus, Thermosphaera aggregans, Pyrodictium occultum P. abyssi, P. brockii, Hyperthermus butylicus, Thermodiscus maritimus, Pyrolobus fumarii, Aeropyrum pernixa, Caldococcus litoralis, Thermococcale, Palaeococcus ferrophilus, Thermococcus aggregans, T. barophilus, T. guaymasensis, T. celer, T. acidaminovorans, T. chitonophagus, T. barossii, T. litoralis, T. profundus, T. stetteri, T. hydrothermalisb, Pyrococcus furiosusb, P. woesei, P. abyssi, P. horikoshiia, Archaeoglobus fulgidusa, A. profundus, Methanococcus jannaschiia, M. vulcanius, M. fervens, M. igneus, M. infernus, Methanothermus fervidus, M. sociabilis, Chaetomium thermophilum, Fervidobacterium islandicum, F. pennivorans, Borrelia burgdorferi, Geobacillus caldoproteolyticus, Thermoanaerobacter yonseiensis,* and *Methanopyrus kandleri* among others. In other examples, the heat-stable proteolytic enzyme is a modified protease that is active at elevated temperatures, such as a modified trypsin (see e.g., Venkatesh and Sundaram, *Protein Eng.* 11:691-698, 1998).

In other examples, protein hydrolysis is increased using catalytic nucleic acids (such as catalytic RNA (ribozymes) or catalytic DNA (deoxyribozymes)) capable of cleaving peptide bonds. See e.g., U.S. Pat. No. 6,063,566; Dai et al., *Science* 267:237-240, 1995. One of skill in the art can identify additional catalytic RNA or DNA capable of cleaving peptide bonds (see e.g. U.S. Pat. No. 6,063,566). In further examples, the chemical additive that increases protein hydrolysis includes one or more catalytic antibodies (see e.g. U.S. Pat. No. 5,258,289).

In some examples, the tissue is hydrated in a liquid solution including Tris (such as about 20-100 mM Tris, for example, 20, 30, 40, 50, 60, 70, 80, 90, or 100 mM) and SDS (such as about 1-5% SDS). In a particular example, the tissue is hydrated in a liquid solution including 50 mM Tris and 2% SDS. In some examples, the liquid solution includes 50 mM Tris, 2% SDS, and 0.2 M glycine. In other examples, the tissue is hydrated in a liquid solution including citrate (such as about 5-100 mM citrate, for example, about 10, 20, 50, or 100 mM). In particular examples, the liquid solution includes 10 mM citrate and 0.05% TWEEN® 20 detergent. In other examples, the tissue is hydrated in a liquid solution including an organic acid, for example, formic acid. In another example, the tissue is hydrated in a liquid solution including 6 M guanidine-HCl. In additional examples, the tissue is hydrated in a liquid solution suitable for standard antigen retrieval methods (see, e.g., Shi et al., *J. Histochem. Cytochem.* 41:1599-1604, 1993; Shi et al., *J. Histochem. Cytochem.* 45:327-344, 1997).

The tissue specimen may be subjected to elevated temperature and pressure by placing the hydrated sample (such as a vial of liquid that contains the tissue specimen, such as homogenized tissue) in a closed vessel having a pumping system such as an air or inert gas hydraulic process, or a high-pressure generator such as a manually operated piston screw pump (e.g., FIGS. 1A and 1B). The pressure of the pumping system or high-pressure generator can be increased using gas boosters or hydraulic intensifiers. Manufacturers of complete high-pressure systems and individual system components include Pressure BioSciences, Inc. (South Easton, Mass.), High-Pressure Equipment Company (Erie, Pa.), and AppliTech Corporation (Lancaster, Pa.).

The sample in the device can be subjected to elevated pressure greater than 1000, 5000, 10,000, 15,000 or 40,000 psi, for example between 1,000 and 100,000 psi, preferably between 10,000 or 15,000 and 75,000 psi, most preferably, between 10,000 and 50,000 psi, for example 40,000 to 45,000 psi. The device can subject the sample to an elevated temperature that is greater than room temperature, for example between 24 and 120° C., such as between 24 and 100° C., for example between 24 and 80° C., such as 60° C., 80° C., or 100° C.

The period of time over which the device applies the elevated pressure and temperature is sufficient to reverse a plurality of the cross-linking formed by the cross-linking agents without substantially denaturing the proteins in the sample. For example, the sample is maintained in the device at the elevated temperature and pressure for at least 15 minutes (such as at least 30 minutes, at least 1 hour, at least 2 hours, for example, about 15 minutes to 24 hours) and/or no more than 24 hours, for example between 15 minutes and 24 hours, between 15 minutes and 18 hours, between 15 minutes and 12 hours, between 15 minutes and 3 hours, or between 15 minutes and 2 hours. In particular examples, the sample is subjected to an elevated pressure for about 2 hours at 80° C. or about 2 hours at 100° C. In some examples, the period of time is adjusted with respect to the temperature (for example, increasing the time with decreasing temperature, such as temperatures less than 80° C.), the size of the sample (for example, decreasing the time with thinner samples, such as a thin tissue sample, for example a tissue section less than 50 μm thick), or the length of time of fixation of the sample (for example, increasing the time with a sample with longer fixation time, such as a sample fixed for more than 24 hours). One of skill in the art can modify the time of application of the elevated pressure to the sample based on the present disclosure (including the Examples, provided below).

The method of recovering biological molecules from the sample permits analysis of the biological molecules from the fixed tissue specimens. For example, the recovered biological molecules are proteins, including antibodies, from formalin-fixed paraffin embedded tissue, and the recovered proteins are used in proteomic studies. Alternatively, the recovered biological molecules are deoxyribonucleic acids or ribonucleic acids from formalin-fixed paraffin embedded tissue, and the recovered deoxyribonucleic acids or ribonucleic acids are used in genomic studies. In yet other examples, the recovered biological molecules are glycoproteins or carbohydrates from formalin-fixed paraffin embedded tissue, and the recovered glycoproteins are used in glycomics studies. In another example, the recovered biological molecules originate from pathogens present in formalin-fixed paraffin embedded tissue and the biological molecules are used for disease studies. In other examples, the recovered biological molecules are antibodies from formalin-fixed paraffin embedded tissue and the recovered antibodies are used in immunological studies. In further examples, the recovered biological molecules are enzymes from formalin-fixed paraffin-embedded tissue and the recovered enzymes are used in enzyme activity studies.

The inventors have recently developed a procedure for the formation of a "tissue surrogate" as a model system for studying protein recovery from archival FFPE tissues, which can be used to quickly evaluate the efficacy of tissue extraction protocols for proteomic studies. That method is disclosed in Fowler et al., *Laboratory Investigation* 87:836-846, 2007, which is incorporated by reference herein. In that publication, high concentrations of cytoplasmic proteins, such as lysozyme and ribonuclease A, were fixed with 10% neutral-buffered formalin. The resulting opaque gel was processed through graded alcohols, xylene, and then paraffin embedding according to standard histological procedures. Tissue extraction protocols in the presence of detergents and heat gave efficient protein extraction from the tissue surrogates, but they failed to reverse most formaldehyde-induced protein modifications. The new methods disclosed herein demonstrate that elevated temperature together with elevated hydrostatic pressure facilitates both protein extraction and reversal of formaldehyde-induced protein modifications from an FFPE tissue specimen.

Example 1

Pressure-Assisted Molecular Recovery (PAMR) of Lysozyme from Tissue Surrogate

The following is a description of the PAMR of the lysozyme protein from a tissue surrogate, which is used as a model system to study the behavior of FFPE tissues.

Materials:

A tissue surrogate is a model system used to study the behavior of FFPE tissues. Hen egg white lysozyme, SDS, and Tris buffer were purchased from Sigma-Aldrich Chemical Company (St. Louis, Mo.). Aqueous 37% (w/v) formaldehyde and xylene were purchased from Fisher Scientific (Pittsburgh, Pa.). Absolute ethanol was purchased from Pharmco-AAPER (Brookfield, Ill.) and PARAPLAST® (paraffin) tissue embedding medium was purchased from Oxford Labware (St. Louis, Mo.).

Figure 2:
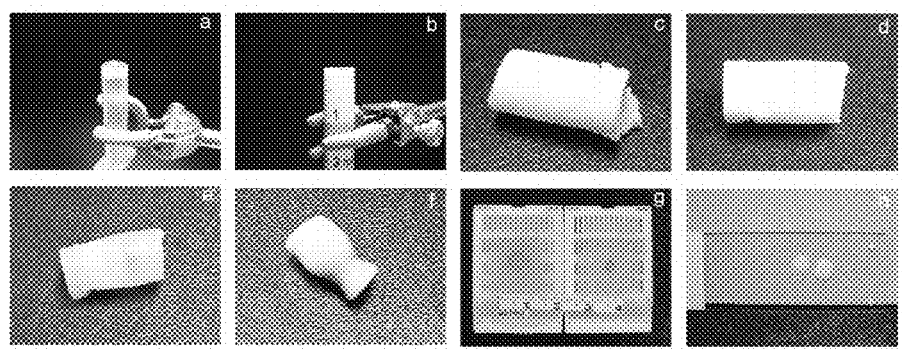
FIG. 2 is a series of digital images demonstrating the formation of a fixed tissue surrogate specimen using the protein hen egg white lysozyme. The photographs depict the solution of lysozyme (150 mg/ml) immediately after mixing with a equal volume of 20% formalin in an open-ended plastic syringe (FIG. 2A); the mixture after 24 hours of fixation (FIG. 2B); the lysozyme tissue surrogate extruded from the syringe (FIG. 2C); the tissue surrogate after processing through a graded series of alcohols (FIG. 2D); the tissue surrogate after processing in xylene (FIG. 2E); the tissue surrogate after incubation overnight in hot liquid paraffin (FIG. 2F); lysozyme tissue surrogates after embedding in a paraffin block for sectioning by a microtome (FIG. 2G); and a pair of lysozyme tissue surrogates after 50-micron sectioning and mounting on a glass slide (FIG. 2H).

Formation of Tissue Surrogates:

The tissue surrogates were formed by mixing a solution of lysozyme at a concentration of 150 mg/ml in deionized water with an equal volume of 20% phosphate-buffered formalin using the following procedure. The end of a 2-ml disposable syringe was removed to create and open-ended tube (FIG. 2A). The syringe barrel was drawn back to the 1-ml mark, and 500 μl of the cytoplasmic protein solution was dispensed into the open end of the syringe. An equal volume of 20% formaldehyde in 20 mM phosphate buffer, pH 7.4, was then added to the syringe and rapidly mixed with the protein solution. An opaque gel formed within 2 minutes, and the resulting surrogate was allowed to stand at room temperature for at least 24 hours to complete the fixation process (FIG. 2B).

Dehydration and Paraffin-Embedding:

The solid, fixed tissue surrogate was ejected from the syringe barrel (FIG. 2C). Dehydration and paraffin-embedding were then conducted by the following protocol. The tissue surrogate was washed with distilled water and then dehydrated through a series of graded alcohols: 70% ethanol for 10 minutes; 85% ethanol for 10 minutes; 100% ethanol for 10 minutes; and a final 100% ethanol dehydration for 10 minutes (FIG. 2D). The tissue surrogate was then incubated through two changes of xylene, 10 minutes each (FIG. 2E), and placed in hot liquid paraffin overnight (FIG. 2F). The processed surrogates were embedded into a tissue cassette using a TISSUE-TEK® embedding console (Miles Scientific, Naperville, Ill., USA) and cooled until the paraffin hardened (FIG. 2G). The tissue surrogate can be sectioned, if desired, as shown in FIG. 2H.

Deparaffinization and Rehydration:

Fifty-micron sections of paraffin-embedded tissue surrogate were transferred to 1.5-ml polypropylene microcentrifuge tubes and deparaffinized by removing the gross excess paraffin and then incubating the surrogate in two changes of xylene for 10 minutes each. The surrogates were rehydrated through a series of graded alcohols for 10 minutes each: 100% ethanol, 100% ethanol, 85% ethanol, and 70% ethanol. The paraffin-cleared surrogates were then incubated in distilled water for a minimum of 30 minutes.

Dispersing the Tissue Surrogate in Solution:

The rehydrated "tissue surrogates" were resuspended in 20 mM Tris, pH 4, 2% (w/v) SDS. The surrogates were then homogenized with a disposable pellet pestle (Kontes Scientific, Vineland, N.J., USA), followed by two 10-sec cycles of sonication on ice using a Sonic Dismembrator, model 550, fitted with a 0.125-inch tapered microtip (Fisher Scientific).

PAMR of the Tissue Surrogate:

A volume of 2 ml of the homogeneous tissue surrogate solution was injected into a pressure cell like that shown in FIG. 1B. The temperature was adjusted to 80° C. and allowed to equilibrate for 15 minutes. The pressure was then increased to 45,000 psi and the solution was incubated at this pressure for 2 hours. The pressure was then slowly released and the processed tissue surrogate solution was withdrawn with a syringe. Any remaining unsolubilized material was pelleted by centrifugation at 14,000×g for 20 minutes, and the supernatant was saved for further analysis.

Analysis of PAMR Results by SDS-PAGE:

The composition of all surrogate preparations was characterized by electrophoresis of dithiothreitol-treated samples in the presence of 0.1% SDS. SDS-polyacrylamide gel electrophoresis (PAGE) was performed on precast NuPAGE Bis-Tris 4-12% gradient polyacrylamide gels (1×80×80 mm) using 2-(N-morpholino)ethanesulfonic acid-SDS running buffer at pH 7.3 (Invitrogen, Carlsbad, Calif., USA). Molecular mass standards and the Coomassie blue-based colloidal staining kit were also purchased from Invitrogen. Gel images were documented using a SCANMAKER™ i900 flat-bed scanner (Microtek, Carson, Calif., USA) and annotated in Adobe PHOTOSHOP® software, version 7.1. The composition of individual gel lanes was analyzed and percentages were determined using UN-SCAN-IT™ Gel 6.1 analysis software (Silk Scientific Corp., Orem, Utah, USA).

Analysis of PAMR Results by Protein Assay:

The total protein content in the recovered reaction supernatant was assessed colorimetrically using a Pierce BCA protein assay (Rockford, Ill., USA) according to a standard microplate protocol. The standard curve was generated using bovine serum albumin standards (25-2000 mg/ml working concentrations). Samples containing reducing agents were assessed using a non-interfering protein assay kit from EMD Biosciences (San Diego, Calif., USA). The absorbance of all samples was read on a SPECTRAMAX® M5 microplate spectrophotometer (Molecular Devices, Sunnyvale, Calif., USA). Percent recovery was calculated relative to an aliquot of the non-formalin-treated original protein solutions.

Analysis of PAMR Results by Mass Spectrometry:

SDS-PAGE Protein gel bands were digested with trypsin, and the peptides were extracted as described in Shevchenko et al. *Analytical Chemistry* 68:850-858, 1996. Samples were desalted with C18 ZIPTIP® pipette tips (Millipore, Billerica, Mass.) according to the manufacturer's protocols and stored at −20° C. until mass spectrometry analysis. Samples (0.5 μl) were co-crystallized with 0.5 μl of α-cyano-4-hydroxycinnamic acid in 50% acetonitrile/1% trifluoroacetic acid and spotted directly on a stainless steel matrix-assisted laser desorption ionization (MALDI) target plate. Mass spectra were acquired by using an Applied Biosystems 4700 MALDI-TOF/TOF (tandem time-of-flight) mass spectrometer (Applied Biosystems, Foster City, Calif.). For all mass spectra the laser frequency was 200 Hz, and for collision-induced dissociation the collision energy was 1 keV (1 eV=1.602×10$^{-19}$J) (air was used as collision gas). The MALDI-TOF/TOF spectra were internally calibrated (<20 ppm) by using trypsin autolysis products. Post-acquisition baseline correction and smoothing was carried out by using software provided with the instrument. Bioinformatic analysis was carried out by using global proteome surveyor (GPS) software (Applied Biosystems).

Figure 3:
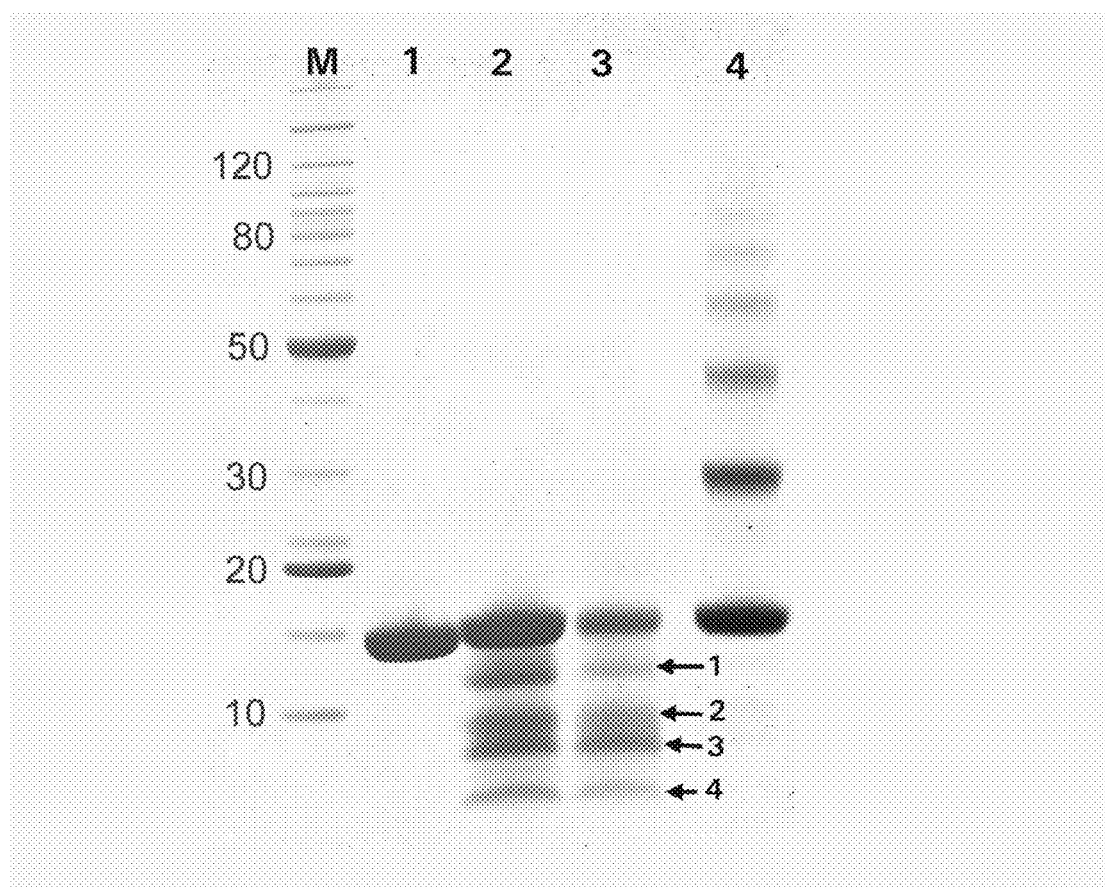
FIG. 3 is a digital image showing SDS-polyacrylamide gel electrophoresis profiles of lysozyme before and after pressure assisted molecular recovery (PAMR) treatment: (lane M) protein molecular weight ladder, (lane 1) native lysozyme in 20 mM Tris, pH 7.4, (lane 2) native lysozyme from lane 1 heated at 80° C. for 2 hours at atmospheric pressure, (lane 3) lysozyme tissue surrogate in 20 mM Tris, 2% (w/v) SDS, pH 4, heated at 80° C. for 2 hours at 45,000 psi pressure, (lane 4) the lysozyme tissue surrogate of lane 3 prior to PAMR. Gel bands 1-4 running below lysozyme in lanes 2 and 3 are peptide fragments resulting from acid-catalyzed cleavage at aspartic acid residues.

Results (SDS-PAGE and Protein Assay):

The gel electrophoresis profile of native lysozyme is shown in FIG. 3 (lane 1). As shown in FIG. 3 (lane 4) a solution of lysozyme tissue surrogate suspended in 20 mM Tris, 2% SDS, pH 4 prior to PAMR contained monomeric lysozyme (lowest band) and species of cross-linked proteins corresponding to dimers through octamers. The same lysozyme sample exposed to 45,000 psi pressure at 80° C. for 2 hours following suspension in 20 mM Tris, 2% SDS, pH 4 showed a complete loss of cross-linked proteins (lane 3) and regeneration of lysozyme monomer. There were 4 gel bands that ran below the monomeric lysozyme (lane 3) that corresponded to lysozyme fragments cleaved at the aspartic acid residues. Such fragments result from acid-catalyzed hydrolysis of aspartate residues when proteins are heated above 70° C. below pH 5. Identical aspartate cleavage products were seen in native lysozyme heated at 80° C. in 20 mM Tris, pH 4 buffer at ambient pressure (lane 2). These cleavage products do not interfere with the identification of the protein by mass spectrometry (below). Lane M is a reference protein molecular weight ladder. Analysis of the solution recovered after PAMR indicated that 95% of the lysozyme was recovered in the solution, with only 5% lost as an insoluble pellet.

Results (Mass Spectrometry):

A mass spectrometric analysis was performed on the lysozyme tissue surrogate after PAMR. The mass spectrometric data were analyzed using NIH bioinformatics tools, and was correctly identified as lysozyme from hen egg white. The results indicated 71% sequence coverage of the recovered lysozyme, which compares favorably with mass spectrometric analysis of native lysozyme. The bioinformatics search of the mass spectrometry data yielded a Mowse probability score of 75, which indicated that the match to hen egg white lysozyme was well above the limit for that observed for a random event (p<0.05). In summary, the mass spectrometry data on the lysozyme recovered from tissue surrogates processed using the PAMR method indicated that formaldehyde cross-links and adducts were successfully reversed by the process. The following is a list of the trypsin digest peptides identified as matching those of native hen egg white lysozyme:

```
                    RUN 1 (matched peptides are underlined)

1 KVFGRCELAA AMKRHGLDNY RGYSLGNWVC AAKFESNFNT QATNRNTDGS

51 TDYGILQINS RWWCNDGRTP GSRNLCNIPC SALLSSDITA SVNCAKKIVS

101 DGNGMNAWVA WRNRCKGTDV QAWIRGCRL  (SEQ ID NO: 1)
```

| Start-End (SEQ ID NO: 1) | Mr(obs) | Mr(expt) | ppm | Sequence |
|---|---|---|---|---|
| 1-5 | 606.3987 | 605.3914 | 44 | -.KVFGR.C |
| 14-21 | 1030.5515 | 1029.5442 | 33 | K.RHGLDNYR.G |

| | | | | |
|---|---|---|---|---|
| 15-21 | 874.4561 | 873.4488 | 45 | R.HGLDNYR.G |
| 34-45 | 1428.7069 | 1427.6996 | 40 | K.FESNFNTQATNR.N |
| 46-61 | 1753.9102 | 1752.9029 | 43 | R.NTDGSTDYGILQINSR.W |
| 62-68 | 936.3743 | 935.3670 | -4 | R.WWCNDGR.T |
| 69-73 | 517.3103 | 516.3030 | 72 | R.TPGSR.N |
| 98-112 | 1675.8430 | 1674.8357 | 25 | K.IVSDGNGMNAWVAWR.N |
| 98-112 | 1691.8544 | 1690.8471 | 35 | K.IVSDGNGMNAWVAWR.N |

RUN 2 (matched peptides are underlined)

```
  1 MRSLLILVLC FLPLAALGKV FGRCELAAAM KRHGLDNYRG YSLGNWVCAA
 51 KFESNFNTQA TNRNTDGSTD YGILQINSRW WCNDGRTPGS RNLCNIPCSA
101 LLSSDITASV NCAKKIVSDG NGMNAWVAWR NRCKGTDVQA WIRGCRL  (SEQ ID NO: 2)
```

| Start-End (SEQ ID NO: 2) | Mr(obs) | Mr(expt) | ppm | Sequence |
|---|---|---|---|---|
| 33-39 | 874.4706 | 873.4633 | 62 | R.HGLDNYR.G |
| 52-63 | 1428.7179 | 1427.7106 | 47 | K.FESNFNTQATNR.N |
| 64-79 | 1753.9088 | 1752.9015 | 42 | R.NTDGSTDYGILQINSR.W |
| 80-86 | 936.4183 | 935.4110 | 43 | R.WWCNDGR.T |
| 87-91 | 517.3118 | 516.3045 | 75 | R.TPGSR.N |
| 135-143 | 1045.6000 | 1044.5927 | 55 | K.GTDVQAWIR.G |
| 144-146 | 335.1386 | 334.1313 | -33 | R.GCR.L |

Example 2

Figure 4:
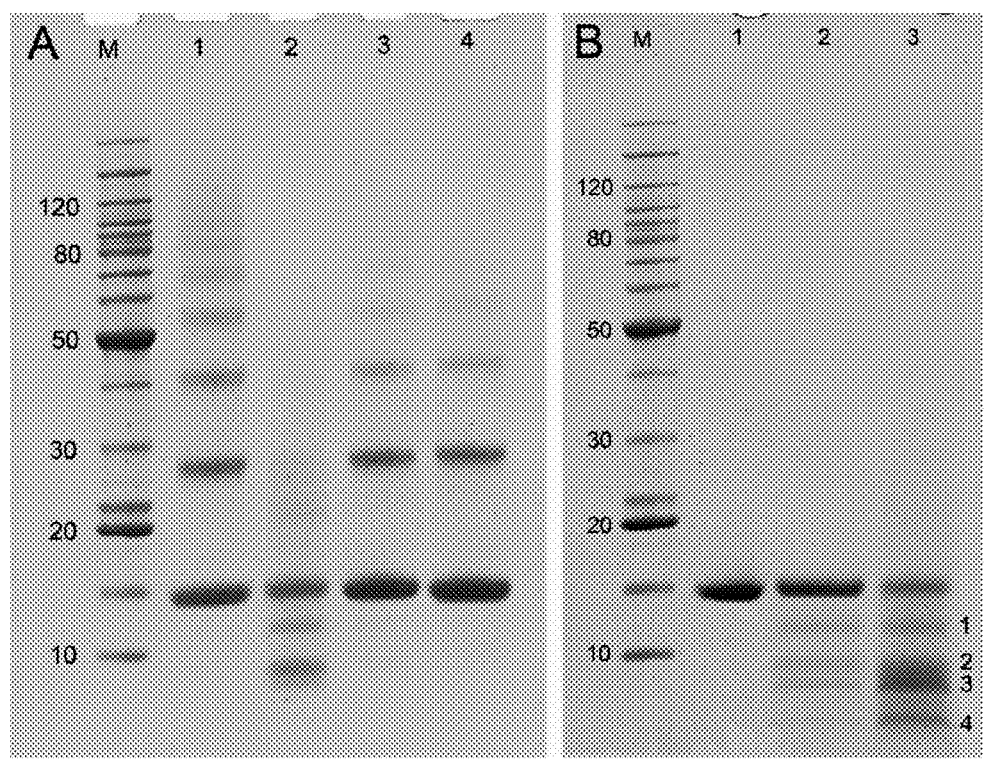
FIG. 4 is a pair of digital images showing electrophoresis gels that illustrate the effect of pH and pressure on the reversal of formaldehyde-induced protein modifications. Lane M; molecular weight markers. (A) SDS-PAGE of FFPE tissue surrogates extracted in 20 mM Tris HCl, with 0.2 M glycine and 2% SDS at 80° C. for 2 h at pH 4 at atmospheric pressure (lane 1); at pH 4 at 43,500 psi (lane 2); at pH 6 at 43,500 psi (lane 3); at pH 9 at 43,500 psi (lane 4). (B) Heating at pH 4 promotes hydrolysis of lysozyme at aspartic acid residues as revealed by SDS-PAGE. Unheated lysozyme (lane 1); non-formaldehyde-treated lysozyme heated at 100° C. for 1 hour (lane 2); FFPE lysozyme tissue surrogate extracted at pH 4 at 45,000 psi and 80° C. for 18 hours (lane 3).

The Effect of Different Elevated Hydrostatic Pressures and Temperatures on the Extraction of Protein from Tissue Specimens Samples of the lysozyme FFPE tissue surrogate (1.5 mg each) were rehydrated and resuspended in 20 mM Tris HCl buffer, pH 4, containing 0.2 M glycine and 2% SDS. When heated at 80° C. for 2 hours at ambient pressure, approximately 60% of the total protein was extracted from the lysozyme surrogate (Table 1). These protein extraction conditions were chosen for their extraction efficiency. However, when analyzed by SDS-PAGE, the total extract was highly cross-linked, with the total protein content corresponding to approximately 20% monomeric, 22% dimeric, 18% trimeric, 15% tetrameric, 12% pentameric, and 13% hexameric species (FIG. 4A, lane 1, and Table 1). In contrast, when the surrogate suspension was heated at 80° C. for 2 hours at elevated pressures (3000 bar or 43,500 psi), 100% of the protein was recovered in the soluble phase. In addition, complete reversal of the formaldehyde-induced intermolecular cross-links was observed (FIG. 4A, lane 2); 42% of total protein content corresponded to monomeric protein and only 1-2% of oligomeric protein (mostly dimer) was present. The remaining gel bands consisted of hydrolytic peptide fragments migrating below the monomer band.

A similar electrophoretic pattern was observed for non-formaldehyde-treated lysozyme heated at 100° C. for 1 hour at ambient pressure (FIG. 4B, lane 2). The gel profile of unheated, non-fixed lysozyme is shown in FIG. 4B, lane 1 for reference. The hydrolytic peptide fragments have been shown to arise from thermally induced cleavage at aspartic acid residues. Given the approximate mass of the four observed peptides, the two intense bands found both in this specimen and in specimens heated at 80° C. for 18 hours at 45,000 psi (indicated in FIG. 4B, lane 3, as bands 2 and 3) correspond to peptides that result from cleavage of aspartic acid residue 66, and the two less intense bands (1 and 4) correspond to peptides that result from cleavage of aspartic acid residue 48, 52, or 87.

TABLE 1

Effect of pressure, temperature, and buffer composition on the recovery of lysozyme from FFPE tissue surrogates

| Figure (lane) | Buffer | Pressure (psi) | Temperature/ Time | % Protein recovered | % Monomer | % Asp cleavages | % Olig- omers |
|---|---|---|---|---|---|---|---|
| *Effect of pressure* | | | | | | | |
| 4A (1) | Tris + SDS, pH 4 | 14.7** | 80° C./2 h | 60% | 20% | none | 80% |
| 4A (2) | Tris + SDS, pH 4* | 43,500 | 80° C./2 h | ~100% | 42% | 58% | none |
| *Effect of pH* | | | | | | | |
| 4A (2) | Tris + SDS, pH 4* | 43,500 | 80° C./2 h | ~100% | 42% | 58% | none |
| 4A (3) | Tris + SDS, pH 6* | 43,500 | 80° C./2 h | ~100% | 31% | none | 69% |
| 4A (4) | Tris + SDS, pH 9* | 43,500 | 80° C./2 h | ~100% | 32% | none | 68% |
| *Effect of temperature and time* | | | | | | | |
| 5A (1) | Tris + SDS, pH 4 | 45,000 | 100° C./2 h | ~100% | 29% | 71% | none |
| not shown | Tris + SDS, pH 4 | 45,000 | 80° C./2 h | 77% | 18% | 39% | 43% |
| 5A (2) | Tris + SDS, pH 4 | 45,000 | 80° C./18 h | ~100% | 27% | 72% | none |
| not shown | Tris + SDS pH 4 | 45,000 | 65° C./2 h | 21% | 31% | 20% | 49% |
| 5A (3) | Tris + SDS, pH 4 | 45,000 | 65° C./18 h | 60% | 34% | 42% | 24% |
| *Effect of additives* | | | | | | | |
| 5B (1) | Tris + SDS + 10 mM CuCl$_2$, pH 4 | 45,000 | 100° C./2 h | ~100% | 40% | none | 60% |
| 5B (2) | Tris + SDS + 50 mM TMAO, pH 4 | 45,000 | 100° C./2 h | ~100% | 35% | 65% | none |
| 5B (3) | Tris + SDS + 20 mM TMAO + 5 mM CuCl$_2$, pH 4 | 45,000 | 100° C./2 h | ~100% | 40% | 60% | none |
| 5B (4) | Tris + SDS + 20 mM TMAO + 5 mM CuCl$_2$, pH 4 | 45,000 | 65° C./18 h | 80% | 53% | 33% | 13% |
| *Effect of storage conditions (Stored for 8 months prior to recovery)* | | | | | | | |
| not shown | Tris + SDS, pH 4 | 45,000 | 100° C./2 h | ~100% | 95% | 5% | none |

Lysozyme tissue surrogate samples (1.5 mg) that were histologically processed to paraffin-embedding were rehydrated and resuspended in the indicated recovery buffer. Total protein in the supernatants was assessed spectrophotometrically following processing. Percentages of monomer, oligomers, and hydrolytic fragments were determined by integration of each lane of the indicated figure. Tris + SDS = 20-50 mM Tris HCl, with 2% SDS.
*Tissue surrogates processed by Barofold, Inc. All other samples were processed using the pressure system shown in FIG. 1.
**Atmospheric pressure.

Figure 6A:
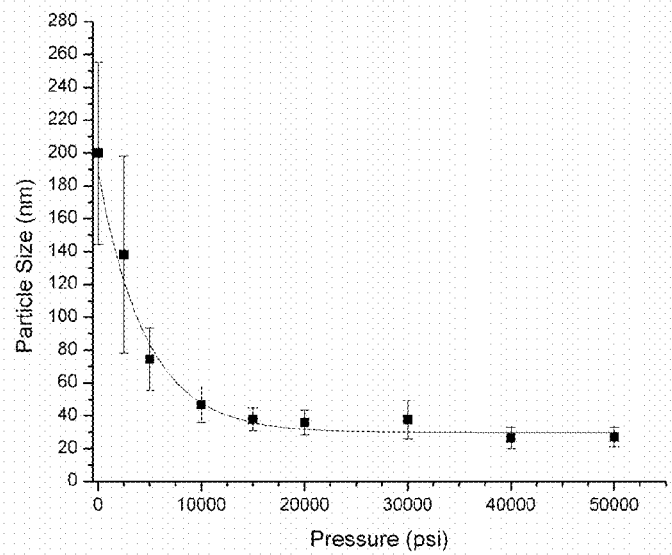
FIG. 6A is a graph showing the effect of pressure on aggregate size of lysozyme tissue surrogate processed at 100° C. for 2 hours.
Figure 6B:
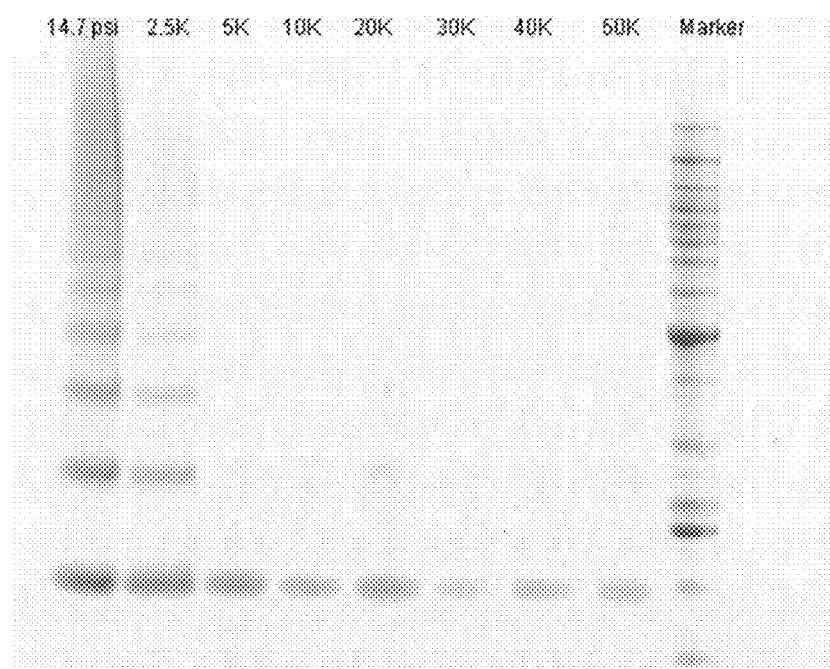
FIG. 6B is a digital image of an electrophoresis gel stained with Coomassie blue showing the effect of the indicated pressures on reversal of formaldehyde crosslinks in lysozyme tissue surrogate.

The lysozyme tissue surrogate was processed at 100° C. for 2 hours at a range of pressures (14.7-50,000 psi) in 50 mM Tris, 2% SDS, 0.2 M glycine, pH 4. Aggregate size was determined by light scattering. Aggregate size was sharply decreased at 10,000 psi and continued to decrease up to 50,000 psi (FIG. 6A). Equal amounts of protein from each treatment (2.5 μg) were also run on an SDS-PAGE gel and stained with Coomassie blue (FIG. 6B).

Example 3

The Effect of Buffer pH on the Extraction of Protein from Tissue Specimens at Elevated Hydrostatic Pressure The inventors previously determined that when tissue surrogates were heated in buffer solutions at 80° C. for 2 hours at ambient pressure, the protein extraction efficiency was dependent upon pH, with 60% of the total protein extracted at pH 4, 51% at pH 6, and 49% at pH 9 (Fowler et al. *Laboratory Investigation* 87:836-846, 2007). In addition, the protein was observed to be highly cross-linked for all three pH values. To determine the effect of elevated hydrostatic pressure and pH, samples of the lysozyme FFPE tissue surrogate (1.5 mg each) were rehydrated and resuspended in 20 mM Tris HCl buffer (pH 4, 6, or 9) containing 0.2 M glycine and 2% SDS. When the surrogate suspensions were heated at 80° C. for 2 hours at elevated pressures (43,500 psi), 100% of the protein was recovered in the soluble phase, regardless of pH (Table 1). However, complete reversal of the formaldehyde-induced intermolecular cross-links was only seen at pH 4 (FIG. 4A, lane 2). Protein oligomers accounted for 69% of the total extracted protein at pH 6 (FIG. 4A, lane 3) and 68% at pH 9 (FIG. 4A, lane 4). Thus, at elevated pressure, protein extraction efficiency is independent of pH, but reversal of formaldehyde-induced protein cross-links is not.

Example 4

Figure 5:
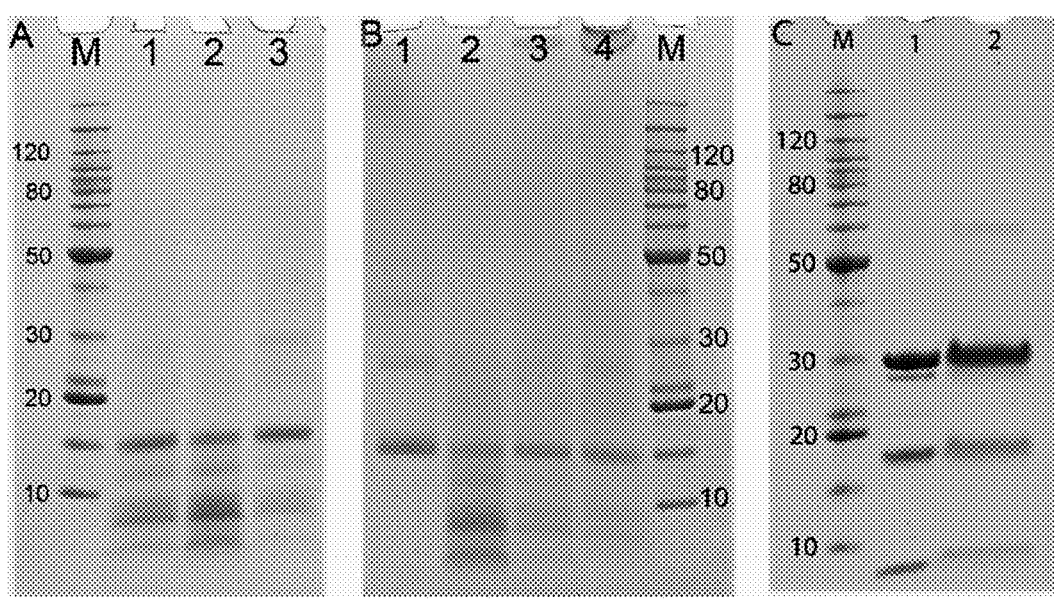
FIG. 5 is a series of digital images showing electrophoresis gels that illustrate the effect of temperature, buffer, and surrogate composition on the reversal of formaldehyde-induced protein modifications and hydrolysis at aspartic acid residues. All surrogates were processed in pH 4 buffer under 45,000 psi of pressure. (A) Effect of temperature. Lane M: molecular weight markers. FFPE tissue surrogate extracted in 50 mM Tris HCl, with 0.2 M glycine and 2% SDS at: 100° C. for 2 hours (lane 1); 80° C. for 18 hours (lane 2); or 65° C. for 18 hours (lane 3). (B) Effect of additives. Tissue surrogates extracted at 100° C. for 2 h in 50 mM Tris HCl, with 2% SDS, and supplemented with 10 mM $CuCl_2$ (lane 1); 50 mM TMAO (lane 2); or 20 mM TMAO and 5 mM $CuCl_2$ (lane 3). Lane 4: Tissue surrogate extracted at 65° C. for 18 h in 50 mM Tris HCl, with 2% SDS, 20 mM TMAO and 5 mM $CuCl_2$. Lane M: molecular weight marker. (C) Extraction of mixed tissue surrogate. 1:1 w/w carbonic anhydrase:lysozyme solution before fixation (lane 1); mixed tissue surrogate after extraction in 50 mM Tris-HCl, with 2% SDS at 65° C. for 18 hours (lane 2). Lane M: molecular weight marker.

The Effect of Temperature and Time on the Extraction of Protein from Tissue Specimens at Elevated Hydrostatic Pressure Samples of the lysozyme FFPE tissue surrogate (1.5 mg each) were rehydrated and resuspended in 20 mM Tris HCl buffer, pH 4, containing 0.2 M glycine and 2% SDS. These suspensions were then processed under elevated pressure (45,000 psi) using protocols differing in incubation temperature and time. Experiments carried out at 45,000 psi were performed with the pressure apparatus shown in FIG. 1. The increase in pressure to 45,000 psi from the 43,000 psi used in the previous experiments is not thermodynamically significant. As shown in Table 1, complete extraction of protein and reversal of formaldehyde-induced protein cross-links was achieved by incubation at 100° C. for 2 hours (FIG. 5A, lane 1) or 80° C. for 18 h (FIG. 5A, lane 2). This demonstrates an inverse relationship between incubation temperature and time for the efficient recovery of protein from the lysozyme tissue surrogate (Table 1). The efficiency of protein extraction by high hydrostatic pressure did not appear to be affected by long term storage of FFPE tissue surrogates. Up to 95% of monomeric lysozyme was recovered from lysozyme tissue surrogates stored in paraffin for up to 8 months (Table 1). Complete protein solubilization and reversal of formaldehyde-induced protein cross-links was difficult to achieve at temperatures below about 75° C., even using long incubation times. For example, incubation for 18 h at 65° C. solubilized only 60% of the protein, which retained a significant level of oligomerization (FIG. 5A, lane 3).

Figure 7:
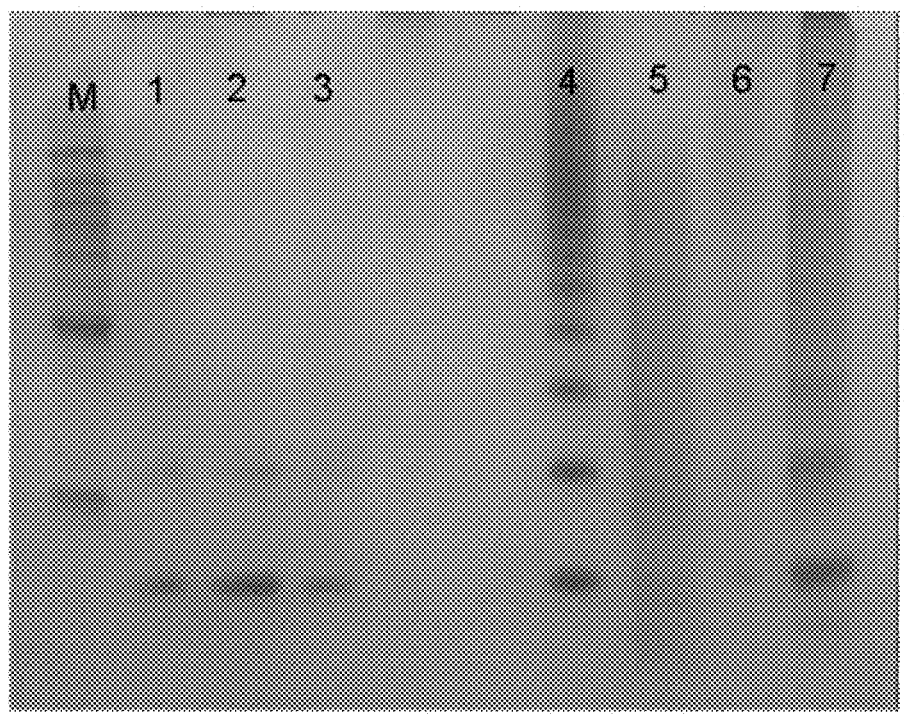
FIG. 7 is a digital image of an electrophoresis gel that illustrates the effect of temperature, time and pressure on the reversal of formaldehyde-induced protein modifications and hydrolysis in lysozyme tissue surrogates. M, molecular weight marker; incubation at 100° C. for 2 hours at 15,000 psi (lane 1), 30,000 psi (lane 2), 60,000 psi (lane 3), and ambient pressure (lane 4) in Tris and SDS at pH 4; incubation at 100° C. for 2 hours in formic acid at 45,000 psi (lane 5), at 60° C. for 2 hours in formic acid at 45,000 psi (lane 6), and 100° C. for 2 hours in formic acid at ambient pressure (lane 7).

FIG. 7 shows the results of similar studies carried out on lysozyme tissue surrogates processed at a variety of elevated temperatures. The illustrated results show improved extraction of protein and reversal of formaldehyde-induced protein cross-links with incubation at 100° C. for 2 hours at 15,000 psi (lane 1), 30,000 psi (lane 2) and 60,000 psi (lane 3) in Tris and SDS at pH 4. Poor reversal of formaldehyde-induced protein cross-links was achieved at the same pH in the same buffers at ambient pressure. Lanes 5-7 show poor reversal of cross-links in 2% formic acid at elevated temperatures.

Additional experiments were performed to assess the effect of varying time and temperature on protein recovery. Lysozyme tissue surrogate was incubated at various temperatures for 2 or 18 hours and protein recovery was determined spectrophotometrically after extraction. Each sample was also analyzed by SDS-PAGE, and gel bands were integrated to determine the percentages of monomers, oligomers, and hydrolytic fragments (Table 2).

were then incubated for 2 hours at 100° C. under an elevated pressure of 45,000 psi. Copper (II) chloride (10 mM) completely suppressed the formation of aspartic acid cleavages (FIG. 5B, lane 1). However, this came at the expense of incomplete reversal of the formaldehyde-induced protein modifications. Treatment with 50 mM TMAO alone (FIG. 5B, lane 2), or in combination with 5 mM copper (II) chloride (FIG. 5B, lane 3), at 100° C. for 2 hours at 45,000 psi slightly suppressed the formation of aspartic acid cleavage peptides and increased the percentage of lysozyme monomer relative to an equivalent sample without either additive (FIG. 5A, lane 1). Finally, the combination of 20 mM TMAO and 5 mM copper (II) chloride significantly suppressed the formation of aspartic acid cleavage products for a tissue surrogate suspension treated at 65° C. for 18 hours at 45,000 psi (FIG. 5B, lane 4). However, the protein extraction efficiency was reduced to 80% and the extract consisted of 13% protein oligomers (mostly dimers).

Although the additives were helpful to reduce cleavage of lysozyme in the tissue surrogate model, mixtures containing several proteins and real tissue specimens do not have significant aspartic acid cleavage and the additives are not believed to be as important for them.

TABLE 2

Effect of temperature and time on protein recovery at elevated pressure

| Buffer | Temp. (Time) | Pressure (psi) | % Recovery | % Monomer | % Oligomers | % Asp Fragments |
|---|---|---|---|---|---|---|
| Tris/2% SDS/0.2M glycine, pH 4 | 80° C. (2 hr) | 14.7* | 60 | 20 | 80 | — |
| Tris/2% SDS/0.2M glycine, pH 4 | 80° C. (2 hr) | 43,500 | 100 | 42 | 1 | 57 |
| Tris/2% SDS/0.2M glycine, (pH 6 or pH 9) | 80° C. (2 hr) | 43,500 | 100 | 30-32 | 68-70 | — |
| Tris/2% SDS/0.2M glycine, pH 4 | 100° C. (2 hr) | 45,000 | 100 | 29 | — | 71 |
| Tris/2% SDS/0.2M glycine, pH 4 | 65° C. (18 hr) | 45,000 | 60 | 34 | 24 | 42 |
| Tris/2% SDS/0.2M glycine, pH 4 | 65° C. (2 hr) | 45,000 | 20 | 23 | 77 | — |
| Tris/2% SDS/ TMAO/CuCl2, pH 4 | 65° C. (18 hr) | 45,000 | 80 | 53 | 13 | 33 |
| Tris/2% SDS/0.2M glycine, pH 4 | 50° C. (18 hr) | 45,000 | 40 | 19 | 81 | — |

*Atmospheric pressure
TMAO: 20 mM, CuCl$_2$: 5 mM

Example 5

The Effect of Additives on the Extraction of Protein from Tissue Specimens at Elevated Hydrostatic Pressure This example demonstrates the effect of various additives for their ability to suppress the formation of peptide cleavage products, such as aspartic acid cleavage peptides, during protein extraction at elevated temperature and pressure. In one example, the osmolyte trimethylamine-N-oxide (TMAO) was chosen based upon its ability to promote structural integrity of the peptide amide linkage at high temperatures (Zou et al. *Journal of the American Chemical Society* 124:1192-1202, 2002), and copper (II) chloride was chosen based upon its ability to form a complex involving the carbonyl oxygen of the amide linkage (Marciani et al. *Analytical Biochemistry* 128:130-137, 1983). Samples of the lysozyme FFPE tissue surrogate (1.5 mg each) were rehydrated and resuspended in 20 mM Tris HCl buffer, pH 4, containing 0.2 M glycine, 2% SDS, plus the additives listed in Table 1. These suspensions Example 6

High-Pressure Extraction of a Mixed Tissue Surrogate

This example demonstrates that high hydrostatic pressure promotes extraction of a representative complement of proteins from a multi-protein system. A previously described mixed tissue surrogate system was used (Fowler et al. *Laboratory Investigation* 87:836-846, 2007). A two-protein tissue surrogate composed of carbonic anhydrase:lysozyme (1:1, w/w) was treated at 45,000 psi for 18 hours at 65° C. (FIG. 5C, lane 2 and Table 3). The recovered solution contained 87% of the total surrogate protein, which was composed of 49% carbonic anhydrase monomer, 39% lysozyme monomer, and ~11% of a putative carbonic anhydrase-lysozyme dimer. The gel profile was almost identical to that of the unfixed protein control solution (FIG. 5C, lane 1). When an identical mixed tissue surrogate was extracted at atmospheric pressure and 65° C., only 25% of the total protein was recovered, which consisted primarily of lysozyme.

TABLE 3

Recovery of a mixed tissue surrogate

| Surrogate composition | Pressure (psi) | Temperature/ time | % total protein recovered | % lysozyme monomer | % carbonic anhydrase | % hetero-dimer |
|---|---|---|---|---|---|---|
| 1:1 lysozyme: carbonic anhydrase | 45,000 | 65° C./18 h | 87% | 39% | 49% | 12% |
| 1:1 lysozyme: carbonic anhydrase | 14.7* | 100° C./20 min/65°/2 h | 81% | 84% | 14% | 2% |

Mixed tissue surrogate samples (1.5 mg) that were histologically processed to paraffin-embedding were rehydrated and resuspended in 50 mM Tris HCl, with 2% SDS, pH 4. Total protein in the supernatants was assessed spectrophotometrically following processing. Percentages of monomer, and oligomers were determined by integration of each lane of the indicated figure.
*Atmospheric pressure.

A five protein tissue surrogate was prepared from 54:15:15:15:1 weight % lysozyme:RNase A: carbonic anhydrase: beta casein:myoglobin. The five protein surrogate was extracted at 45,000 psi and 100° C. for 2 hours in either Tris+2% SDS, pH 4 or 2% (v/v) formic acid, pH 2. The extracts were lyophilized, resuspended in 20% methanol in 50 mM $NH_4HCO_3$, pH 7.9, and digested overnight with trypsin. Sequence coverage was determined by LC-MS/MS. The results indicated 12% sequence coverage of the recovered β-casein extracted in Tris/SDS at pH 4, which compared favorably with mass spectrometric analysis of β-casein in the native tissue surrogate (Table 4).

TABLE 4

Protein coverage map for a five protein tissue surrogate extracted under high hydrostatic pressure

| Condition | Lysozyme | | Carbonic Anhydrase | | Myoglobin | | Ribonuclease A | | β-Casein | |
|---|---|---|---|---|---|---|---|---|---|---|
| | unique peptides/ spectra1 | % Sequence coverage | unique peptides/ spectra | % Sequence coverage | unique peptides/ spectra | % Sequence coverage | unique peptides/ spectra | % Sequence coverage | unique peptides/ spectra | % Sequence coverage |
| Native | 15/24 | 77% | 18/23 | 68% | 15/23 | 85% | 6/7 | 58% | 3/4 | 16% |
| FFPE, Tris + SDS | 6/7 | 48% | 6/7 | 22% | 1/2 | 5% | 1/1 | 14% | 2/2 | 12% |
| FFPE, Formic Acid | 15/23 | 80% | 10/12 | 56% | 12/16 | 73% | 5/6 | 60% | 1/1 | 4% |

The effect of pH was determined by solubilizing the five protein tissue surrogate at 100° C. for 2 hours in 50 mM Tris/2% SDS at pH 4, 7.4, or 9. The total protein content was then determined using a Pierce BCA protein assay. At each pH, extraction at 45,000 psi resulted in a higher protein concentration than extraction at ambient temperature (Table 5). Extraction at pH 9 at 45,000 psi produced the greatest total protein extracted, followed by pH 4, and pH 7.4. 10 μg of each extract was used for analysis on the Agilent 2100 Bioanalyzer using the Protein 230 chip (Agilent, Santa Clara, Calif.) according to the manufacturer's instructions. Recovery of lysozyme and RNase A were fairly consistent at all pHs tested, while myoglobin recovery was higher at pH 4 and β-casein and carbonic anhydrase recovery was higher at pH 7.4 (Table 6).

TABLE 5

Effect of pH and on total protein extraction of five protein tissue surrogate

| Sample | pH (50 mM Tris + 2% SDS) | Extraction Conditions | Conc. (μg/ml) | C/V % |
|---|---|---|---|---|
| 1 | 4 | 100° C., 2 h, 45,000 psi | 802 ± 20 | 2.5 |
| 2 | 4 | 100° C., 2 h, ambient pressure | 675 ± 10.0 | 1.5 |
| 3 | 7.4 | 100° C., 2 h, 45,000 psi | 657 ± 15.1 | 2.3 |

TABLE 5-continued

Effect of pH and on total protein extraction of five protein tissue surrogate

| Sample | pH (50 mM Tris + 2% SDS) | Extraction Conditions | Conc. (μg/ml) | C/V % |
|---|---|---|---|---|
| 4 | 7.4 | 100° C., 2 h, ambient pressure | 379 ± 13.3 | 3.5 |
| 5 | 9 | 100° C., 2 h, 45,000 psi | 933 ± 3.9 | 0.4 |
| 6 | 9 | 100° C. 2 h, ambient pressure | 520 ± 10 | 1.9 |

TABLE 6

Results of integration of Lab on a Chip

| Band size (kDa) | Possible protein ID | % Composition | | | | | |
|---|---|---|---|---|---|---|---|
| | | Sample 1* | Sample 2* | Sample 3* | Sample 4* | Sample 5* | Sample 6* |
| 13-14 | Lysozyme + RNAseA | 71.9 | 68.5 | 69.5 | 69.6 | 67.8 | 60.9 |
| 20 | myoglobin | 4.0 | 4.8 | 3.3 | 2.3 | | 0.7 |
| 25 | b-casein | 17.7 | 15.8 | 17.8 | 17.8 | 24.2 | 17.1 |
| 29 | Carbonic anhydrase | | 1.9 | 2.6 | 1.0 | | 0.5 |
| 35-38 | | 5.6 | 7.1 | 6.1 | 7.8 | | 15.8 |
| 43 | | | 0.3 | 0.7 | 0.4 | 0.4 | 1.9 |
| 50 | | 0.8 | 1.6 | | 1.1 | 1.1 | 2.3 |

*Samples are the same as those shown in Table 4.

Figure 8:
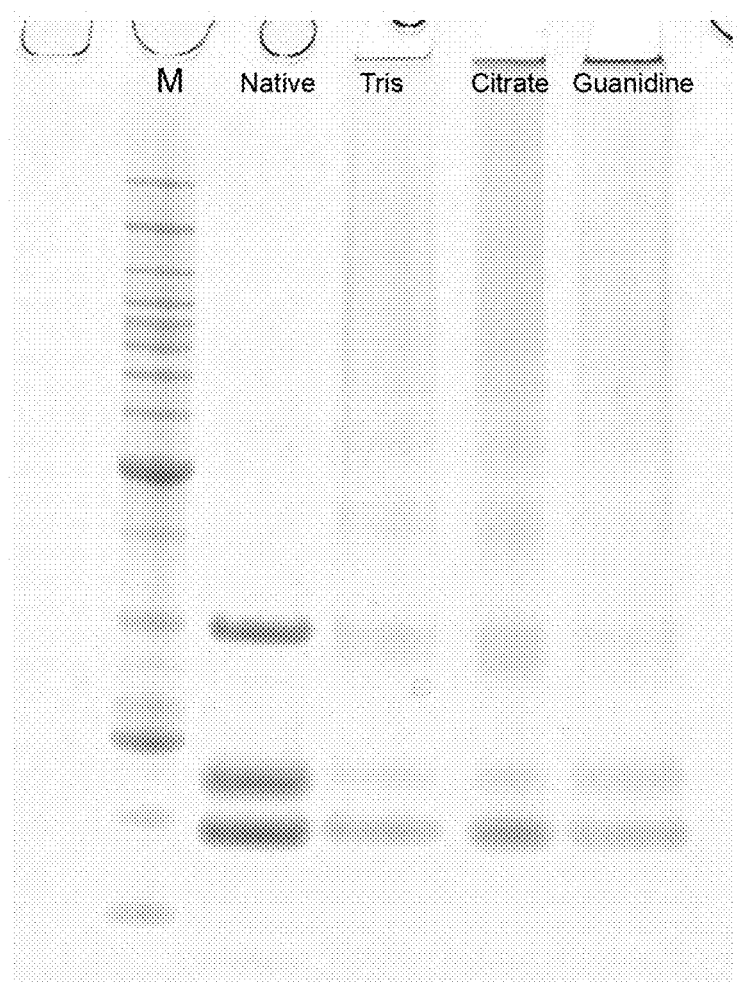
FIG. 8 is a digital image of an electrophoresis gel stained with Coomassie blue showing the effect of various buffers on reversal of formaldehyde crosslinks in multi-protein tissue surrogate.

The effect of different solutions on protein recovery from the five protein tissue surrogate was also tested. The five protein FFPE tissue surrogate was suspended in the indicated solutions and heated at 100° C. for 2 hours at atmospheric pressure or 45,000 psi. Total protein recovery was determined by measuring absorbance at 280 nm. Protein recovery was also assessed by running the samples on an SDS-PAGE gel and staining with Coomassie blue. Each of the tested solutions provided good recovery at 45,000 psi (Table 7 and FIG. 8).

TABLE 7

Protein recovery in different solutions

| Sample | [Lysozyme], mg/ml | % Recovery (relative to native) |
|---|---|---|
| Native | 0.27 | 100% |
| Tris/2% SDS/0.2M glycine, pH 7, 45,000 psi | 0.22 | 81% |
| Tris/2% SDS/0.2M glycine, pH 7, 14.7 psi | 0.04 | 15% |
| 10 mM citrate/0.05% Tween ®-20, pH 6, 45,000 psi | 0.23 | 85% |
| 10 mM citrate/0.05% Tween ®-20, pH 6, 14.7 psi | 0.03 | 11% |
| 6M Guanidine-HCl, pH 6, 45,000 psi | 0.34 | ~100% |
| 6M Guanidine-HCl, pH 6, 14.7 psi | 0.05 | 19% |

The methods disclosed herein demonstrate the efficient extraction of protein and the reversal of formaldehyde-induced protein adducts and cross-links from fixed tissue specimens are possible. In several examples, the extraction and reversal was performed with a FFPE tissue surrogate using heat treatment augmented by elevated hydrostatic pressure. Formaldehyde-induced protein modifications increase protein stability and can raise the thermal denaturation temperature of fixed proteins to temperatures above 100° C. Elevated pressure counteracts this effect, in part, by reducing protein stability through promotion protein unfolding.

Example 7

Extraction of Proteins from Mouse Liver by PAMR

Freshly harvested liver from an 11-week old C57BL/6 mouse was bifurcated, and one-half was frozen overnight at −20° C. in TISSUE-TEK® OCT™ media. The remaining liver tissue was fixed overnight in 10% buffered formalin and then dehydrated through a graded ethanol series, xylenes, and paraffin-embedded according to standard histological methods. Approximately 3 mg of fresh-frozen liver or FFPE liver was homogenized in 8 mL of 50 mM Tris-HCl, pH 4, with 2% (w/v) SDS. The FFPE and fresh homogenates were then heated at 100° C. for 30 minutes, followed by 2 hours at 60° C. or 100° C. for 30 minutes, followed by 2 hours at 80° C. at either atmospheric pressure or under elevated pressure (45,000 psi). After treatment, the protein content of each extract was measured using the Pierce BCA protein assay kit and equal amounts of each sample were separated by SDS-PAGE.

Figure 9:
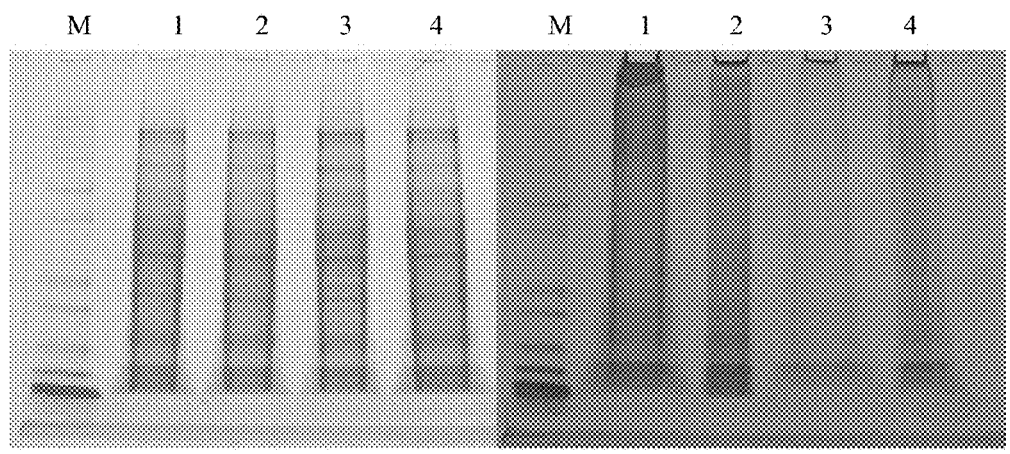
FIG. 9 is a pair of digital images of SDS-PAGE gels of fresh mouse liver (panel A) or FFPE mouse liver (panel B) extracted under the following conditions: Lane 1, 100° C. for 30 minutes, followed by 2 hours at 60° C. at 45,000 psi; lane 2, 100° C. for 30 minutes, followed by 2 hours at 80° C. at 45,000 psi; lane 3, 100° C. for 30 minutes, followed by 2 hours at 60° C. at atmospheric pressure; lane 4, 100° C. for 30 minutes, followed by 2 hours at 80° C. at atmospheric pressure.

The fresh liver homogenate gave rise to multiple, well-resolved protein bands by SDS-PAGE, regardless of the extraction temperature or extraction pressure (FIG. 9A). However, the FFPE liver tissue required significant heating and pressure for protein solubilization. Samples heated at atmospheric pressure (FIG. 9B, lanes 3 and 4) contained relatively fewer well-resolved protein and the total protein content was approximately half that of identical FFPE samples processed at elevated pressure (FIG. 9B, lanes 1 and 2). In particular, the FFPE sample heated at 100° C. for 30 minutes, followed by 2 hours at 80° C. at 45,000 psi exhibited a number of well resolved protein bands relative to its non-pressure treated control (FIG. 9B, lane 4) and the total protein content was comparable to the fresh frozen homogenates (0.34 mg/ml). Additionally, the non-pressure treated samples exhibited significantly less staining than their pressure-treated counterparts. Since the Coomassie-R-250 dye interacts with charged amino acid residues such as arginine, which reacts with formaldehyde, there may be a significant number of formaldehyde-protein adducts and cross-links remaining in the non-pressure treated samples. These results indicate that the application of pressure improves the staining of FFPE tissues over conventional heat-induced antigen retrieval techniques.

In additional experiments, fresh liver was extracted in 50 mM Tris, pH 4 with 2% SDS at 4° C. for 2.5 hours. The FFPE liver was extracted in 50 mM Tris, pH 4 with 2% SDS at 100° C. for 30 min, followed by 80° C. for 2 hours at either atmospheric pressure or 45,000 psi. Then 40 micrograms of each extract was separated by SDS-PAGE and each gel band was divided into about 10 segments, which were analyzed, in duplicate, in 4 fractions each by LC MS/MS. Extraction of FFPE liver at 45,000 psi resulted in recovery of more protein than extraction at atmospheric pressure (Table 8).

TABLE 8

Effect of pressure on recovery of proteins from FFPE mouse liver

| Sample | Treatment condition | Treatment pressure | Unique Protein Identifications |
|---|---|---|---|
| Fresh liver | 100° C., 30 min + 80° C., 2 h | 45,000 psi | 254 |
| Fresh liver | 100° C., 30 min + 80° C., 2 h | Ambient pressure | 203 |
| FFPE liver | 100° C., 30 min + 80° C., 2 h | 45,000 psi | 371 |
| FFPE liver | 100° C., 30 min + 80° C., 2 h | Ambient pressure | 135 |

Example 8

Pressure Instrument

A particular embodiment of a pressure instrument 10 is shown in FIG. 1A for performing the extraction and reversal of proteins from fixed tissue specimens. Instrument 10 includes a small bore cylinder 12 which is associated with a rotatable piston screw pump having a rotatable drive handle 14. A liquid (not shown) is present in cylinder 12 and is capable of being pressurized by rotation of handle 14 to generate pressures of up to 75,000 psi. The generated pressure is measured by pressure gauge 16. An HPLC pump 18 supplies protein extraction buffer into a pressure cylindrical specimen cell 20 (FIG. 1B) through an inlet valve 26 which can be turned off after injection of the buffer. A heating collar 22 helps regulate the temperature of the sample as it is held under pressure, and the temperature is regulated by a thermoregulator 24.

The pressure instrument, as shown in FIGS. 1A and B is simple to use, does not require any proprietary reagents, and can be manufactured at relatively low cost. The pressure instrument permits the extraction of proteins from tissue specimens under elevated pressures and temperature, such as the methods described herein.

FIGS. 10-16 illustrate an embodiment of a reaction chamber 40 for subjecting biological specimens (such as tissue histology specimens) to elevated temperatures and pressure for histological fixation or reversal of cross-links and adducts formed by a tissue fixation process.

Figure 10:
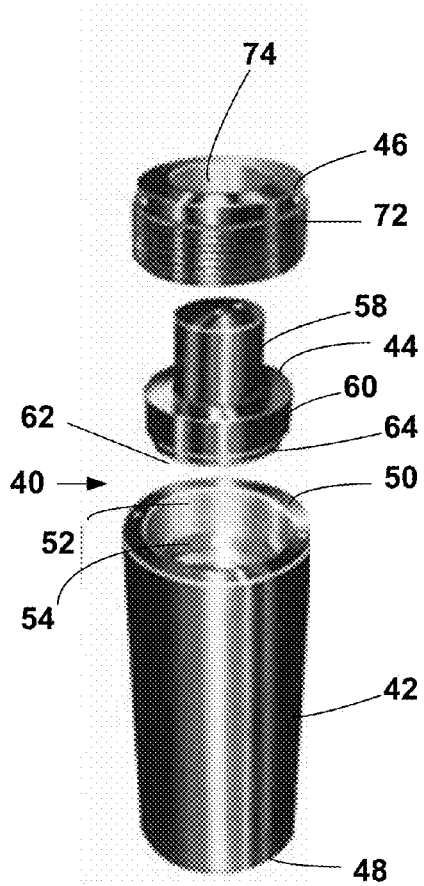
FIG. 10 is a perspective exploded view of an embodiment of a reaction chamber for fixation of specimens under elevated temperature and pressure.
Figure 11A:
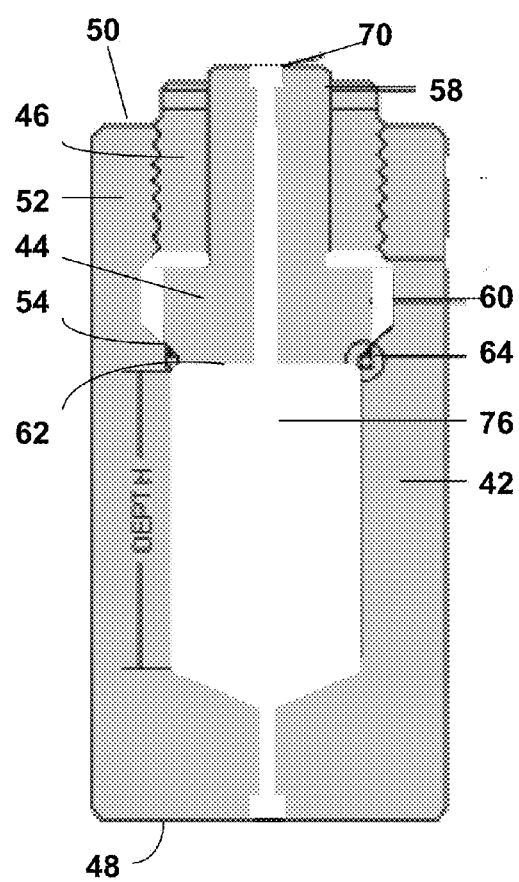
FIG. 11A is a cross-sectional side view of the assembled reaction chamber shown in FIG. 10.
Figure 11B:
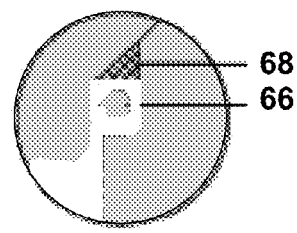
FIG. 11B is an enlarged fragmentary view of FIG. 11A, showing the O-ring seal for the reaction chamber.
Figure 12:
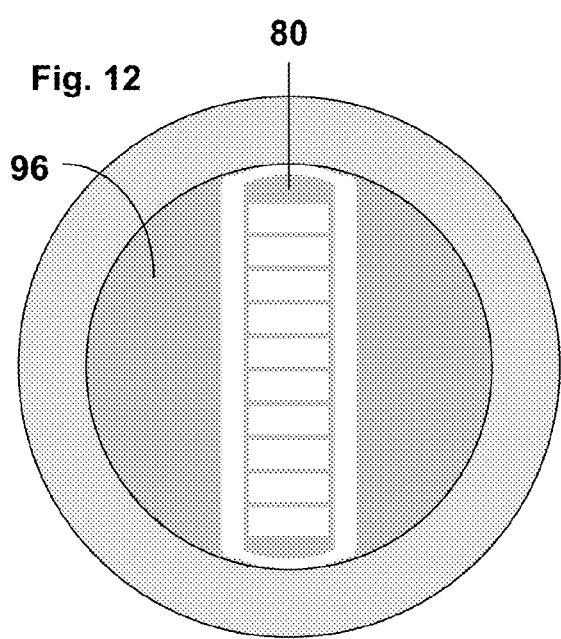
FIG. 12 is a top view of the reaction chamber of FIG. 10 showing a slide tray retained within the reaction chamber and surrounded by a volume reduction block.

FIG. 10 shows a thick-walled stainless steel reaction vessel 42, a cover 44 and a closure nut 46. Reaction vessel 42 is a hollow cylinder made of sufficiently thick material to withstand pressures of at least 5000 psi, for example up to 10,000 psi, 50,000 psi or even 100,000 psi. Reaction vessel 42 has a solid closed bottom wall 48 and an open top 50. The internal wall of reaction vessel 42 adjacent open top 50 has a cylindrical portion 52 that is internally threaded. An internal shoulder 54 is present below internally threaded portion 52, and it tapers the width of reaction vessel 42 from a larger diameter upper portion to a reduced diameter lower portion, thereby providing an angled support surface.

Cover 44 includes an upper reduced diameter projection 58 and a larger diameter base 60. A lower face 62 of base 60 has a peripheral lip that forms an inclined surface that is shaped to cooperatively fit against internal shoulder 54 of reaction vessel 42. A O-ring 64 also extends around the peripheral lip of lower face 62. As shown in greater detail in FIG. 11B, O-ring 64 includes a primary O-ring 66 and a back-up O-ring 68. A pressure connection pathway 70 extends axially through cover 44 from its lower face 62 to a top surface of projection 58.

Closure nut 46 is a ring-shaped member that is provided with external threads 72 that cooperatively mate with the internal threads of cylindrical portion 52 of reaction vessel 42.

In a particular example, the pressure chamber 40 can be purchased from High Pressure Equipment Company of Erie Pa. 16505. An example of a particular model that could be used for this purpose is model R3-6-20.

In use, reaction vessel 42 is sealed by placing cover 44 in open top 50 of reaction vessel 42 with the peripheral lip of inclined lower face 62 resting on internal shoulder 54, and O-ring 64 sealing a pressure chamber 76 that is formed within reaction vessel when cover 44 is in place. Closure nut 46 is then screwed into the open top of reaction vessel 42 so that its external threads 72 mate with internal threads of portion 52 to retain cover 44 in sealed engagement against internal shoulder 54. Pressure connection pathway can then be connected to a source of external pressure (not shown) to maintain pressure chamber 76 at a desired pressure. The reaction vessel can also be placed in a temperature mantle 76 (FIG. 16) that is regulated by a temperature controller 78 to regulate the temperature of reaction vessel 42 at a desired temperature.

Figure 13:
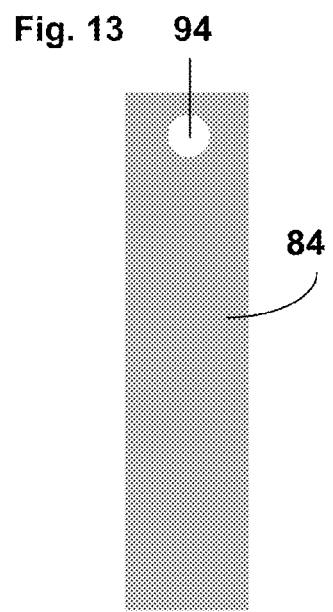
FIG. 13 is an end elevational view of the slide tray.
Figure 14:
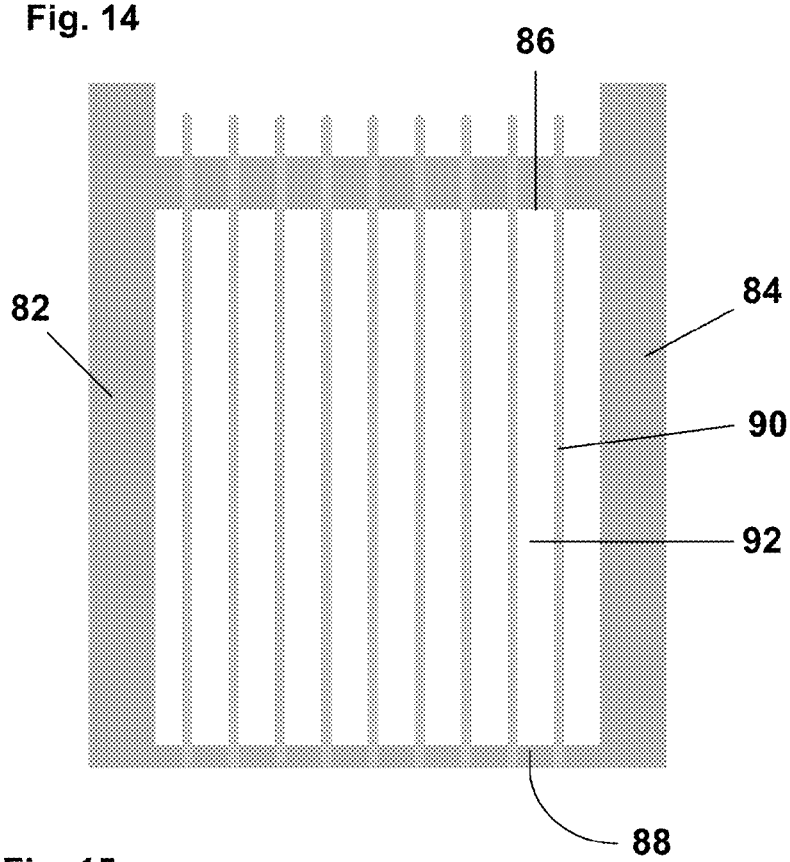
FIG. 14 is a side elevational view of the slide tray of FIG. 13.
Figure 15:
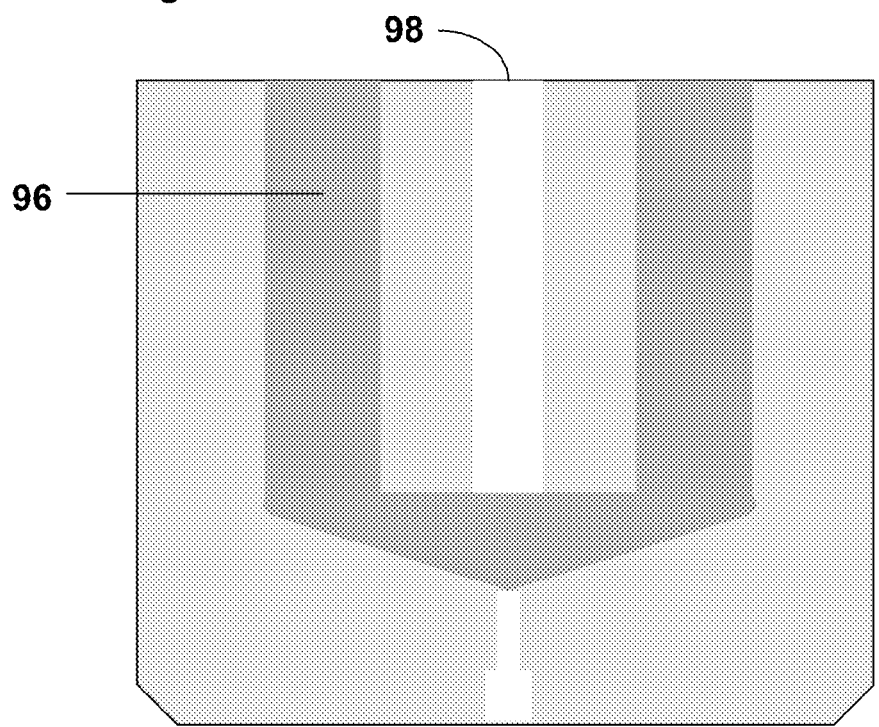
FIG. 15 is a cross-sectional side view of the reaction chamber of FIG. 12 with the volume reduction block inside the reaction chamber, but without the slide tray.
Figure 16:
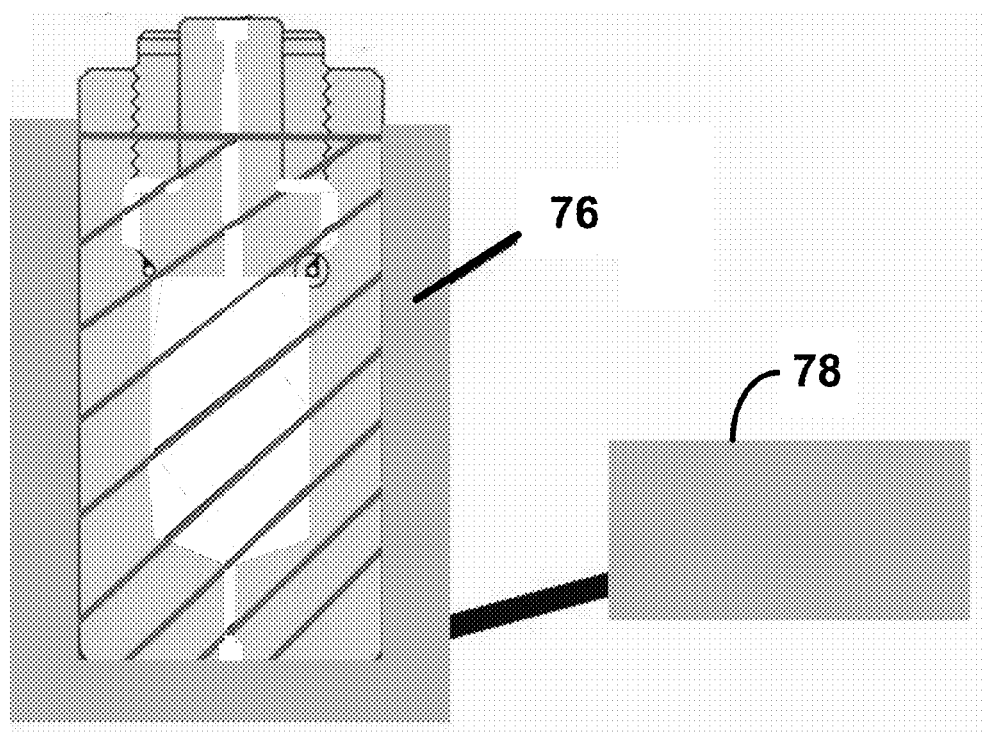
FIG. 16 is a cross-sectional side view of the assembled reaction chamber assembly retained within a heating mantel for subjecting its contents to elevated temperatures and pressures.

An embodiment of the device is shown in FIGS. 12-15 in which a slide tray 80 is retained within reaction vessel 42. As shown in FIGS. 13 and 14, slide tray 80 is formed by side walls 82, 84, upper cross-piece 86 and lower cross-piece 88. A plurality of parallel partitions 90 separate tray 80 into multiple individual slide receptacles 92. In the disclosed embodiment, the holder is 1⅛ inches wide, 2⅞ inches long, and 3⅜ inches deep. The upper and lower metal cross-pieces 86, 88 are 2⅞ inches long and the slide receptacles 92 are separated by approximately 1/16 inches to hold glass slides therebetween. In an alternative embodiment (not shown), tray 80 can be fabricated to hold up to four tissue histology cassettes.

Side walls 82, 84 are provided with a handle hole 94 through which a wire handle (not shown) can be placed to insert tray 80 into and withdraw it from reaction vessel 42. A volume reduction block 96 is also provided to reduce the unused volume of liquid in reaction vessel 42. Block 96 has an external wall that conforms to the internal walls of pressure chamber 76, and an internal receptacle 98 that generally conforms to the shape and size of tray 80.

In operation, block 96 is placed in pressure chamber 76 and tray 80 is inserted into receptacle 98 which is filled with a liquid, such as the liquids described herein for hydration or fixation of a tissue specimen. The reaction vessel is then assembled and pressurized as already described in association with FIGS. 10-11 above.

In other examples, the methods described herein can be carried out using any apparatus capable of maintaining elevated pressures and temperatures for a sufficient period of time to reverse at least a portion of cross-links in a tissue specimen (such as a tissue specimen fixed with a cross-linking agent) or to increase perfusion of a fixative into a tissue specimen. In particular examples, the apparatus can include a pressure cycling reactor (e.g., U.S. Pat. Nos. 6,036,923; 6,635,469; and 6,569,672). The pressure cycling reactor can include a temperature controller (such as a circulating water bath or heating collar) such that the chamber is maintained at the desired temperature (e.g. from about 50° C. to about 100° C.). In one example, the apparatus is a BAROCYCLER® high pressure instrument (Pressure Biosciences, Inc.; South Easton, Mass.).

Example 9

Inhibiting Hydrolysis at Aspartyl Residues

Even at high hydrostatic pressures, elevated temperature provides the energy to reverse formaldehyde-induced protein adducts and cross-links. However, such heat treatment can cause protein modifications. At pH 4, these modifications are deamidation of glutamine and asparagine residues, and n+1 hydrolysis at aspartic acid residues. The MS analysis of lysozyme recovered following treatment at 80° C. and 43,500 psi indicated that deamidation is not a significant problem under these conditions. However, the hydrolysis products running below the lysozyme monomer in FIG. 4B, lane 3, are believed to be peptide fragments produced by aspartic acid hydrolysis.

The mechanism for hydrolysis at aspartyl residues involves an anhydride or a cyclic imide intermediate, formed between the α-carboxyl group and the amide group at either terminal through elimination of one water molecule. The Asp-X bond is most readily cleaved, but the X-Asp may also be cleaved. Thus, the resulting peptides may have at least one aspartyl residue at the point of cleavage, or they may lose the aspartyl residue by a double cleavage event. Lysozyme contains seven aspartic acid residues. When the LC-MS/MS data was analyzed allowing for aspartic acid as a potential cleavage site, fragments arising from cleavage of the aspartic acid n+1 peptide bond at Asp 48 and 52 were identified. Hydrolysis at either of these residues produces peptides of appropriate size for two of the fragments observed by SDS-PAGE (FIG. 4B, lane 3, bands 1 and 4). Cleavage at Asp 66 or Asp 87 may be responsible for the remaining hydrolytic peptides, though these fragments were not identified by MS.

Several additives were investigated for their ability to abrogate aspartic acid hydrolysis, including the amide bond-stabilizing osmolyte TMAO and the amide complexing metal copper (II) chloride. Of these, a combination of 20 mM TMAO and 5 mM copper (II) chloride combined with an extraction temperature of 65° C. for 18 h reduced the amount of hydrolytic fragments to 33% and gave almost quantitative recovery of lysozyme, with the dimeric protein band accounting for 13% of total protein (FIG. 5B, lane 4). Without being bound by theory, it is believed that copper partially interferes with the formation of the anhydride intermediate, thus preventing the peptide bond cleavage at aspartic acid residues, whereas TMAO assists with protein disaggregation. Conditions suppressing aspartic acid cleavage (such as copper (II) chloride and pH values >4) also reduce the reversal of protein formaldehyde modifications (Table 1).

Cleavage at aspartic acid residues does not present an obstacle to proteomic analysis because the chemical hydrolysis takes place at a well-defined location (the aspartic acid n+1 amide bond). Thus, aspartic acid residues can be treated as possible cleavage sites in the bioinformatics analysis of the MS results. In fact, acid-catalyzed chemical cleavage at aspartic acid residues followed by tryptic digestion of the partially degraded protein has been used in the proteomic identification of protease-resistant ribonuclease A by MALDI-MS (de Koning et al., *Eur. J. Biochem.* 273:281-291, 2006).

MS analysis identified 10 tryptic fragments, representing >70% overall sequence coverage. Only two major tryptic fragments, from Gly 22 to Lys 33, and Asn 64 to Lys 86, were unaccounted for. An analysis of the relative distribution of amino acids known to react with formaldehyde throughout the lysozyme sequence did not indicate any residue bias in the unrepresented peptides. Since a number of peptides with four or more reactive amino acid residues were identified by MS, there were no indications that any tryptic fragments were misidentified due to the presence of formaldehyde adducts. A comparison of the peptides observed in the analysis of native and high-pressure FFPE lysozyme tissue surrogates by both MALDI and ESI-MS showed a high degree of overlap. Ten tryptic lysozyme peptides were identified within each sample. Eight of these peptides were in common, with each of the samples containing two uniquely identified peptides. The two peptides unique to the native lysozyme sample, GYSLGNMMVCAAK (SEQ ID NO: 1, residues 22-33) and LCNIPCSALLSSDITASVNCAK (SEQ ID NO: 1, residues 75-96), both had very low signal intensity when the digested protein was analyzed using MALDI, therefore it may not be surprising that they were not observed in the analysis of the FFPE sample.

Example 10

Pressure-Assisted Antigen Retrieval (PAAR)

The Pressure Assisted Molecular Recovery (PAMR) method can be used to retrieve antigens having restored immunogenicity, in which case the method is referred to as a Pressure-Assisted Antigen Retrieval (PAAR) method that also permits recovery of an antigen biomolecule, such as a protein, wherein the immunoreactivity or function of biological molecules present in tissue sections are at least partially restored to their immunoreactivity or function prior to fixation. The restoration of the immunoreactive properties after the biological molecules have been fixed with a cross-linking agent and mounted in tissue sections on a substrate permits the mounted tissue sections to be characterized by immunohistochemistry or functional histochemical assays. The method therefore provides the unexpected advantage of more reliably identifying the presence of antigens in mounted fixed tissue sections using immunohistochemical methods, and identifying the presence of enzymes in mounted fixed tissue sections using enzyme histochemical methods.

The disclosed antigen retrieval method can be used with a variety of fixed tissue specimens. For example, the biomolecules can be recovered from tissue that has been fixed with a cross-linking agent such as formaldehyde, paraformaldehyde, glutaraldehyde, or 1-ethyl-3-(3-dimethylaminopropyl). The cross-linked tissue may have been embedded in a variety of media such as paraffin, paraffin-containing compounds, araldite, celloidin, DURCUPAN™ embedding medium, epoxy, glycol methacrylate, hydroxypropyl methacrylate, JB-4™ embedding medium, Spurr, or LR WHITE™ embedding medium. The fixed tissue specimen may have been placed on a variety of rigid or semi-rigid substrates, such as glass, plastic, metal, and nitrocellulose.

The liquid in which the mounted fixed tissue section is suspended for rehydration is not particularly limited. In disclosed examples, the liquid is selected from the group consisting of water, alcohols, organic solvents, aprotic solvents, protic solvents, organic acids, organic bases, and supercritical fluids. In particularly disclosed examples, the liquid is water, or water-alcohol, solutions containing a buffering agent and additional chemical additives. A variety of buffering agents are suitable for use in the method, for example acetate, phosphate, PBS, citrate, borate, carbonate-bicarbonate, Tris, Tris-acetate-EDTA, Tris-borate, Tris-glycine, HEPES, MES, TAPS, and MOPS. The buffer helps maintain the pH of the water, or water-alcohol, solution between 2 and 12, for example between 4 and 9.

Other features of the recovery method are those described in association with the PAMR method.

Once the tissue specimen has been treated under the disclosed conditions of elevated temperature and pressure to reverse fixation-induced cross-links, the specimen (or a protein retrieved from it) can be subjected to an immunological or other molecular analysis. An example is shown in FIG. 9B, which shows use of elevated temperature and pressure to recover a FFPE mouse liver sample.

Example 11

Immunological and Other Molecular Analysis of Treated Tissue

The tissue specimens can be subjected to a variety of biological analyses, including immunological and nucleic acid analysis. The specimens can be analyzed in an intact form, such as a tissue section, that preserves the cytoarchitecture of the specimen. Alternatively, the specimen can be homogenized for analysis, and/or target molecules (such as protein and/or nucleic acid) extracted for further analysis.

The elevated pressure/temperature methods disclosed herein provide tissue specimens in which antigen is recovered and its antigenicity preserved. The choice of fixative may be optimized for recovery and preservation of particular antigens. Non-specific binding sites are blocked, antigen is bound by specific antibody (e.g., the primary antibody), and non-bound antibody is removed. If labeled with a probe or signal generating moiety, the primary antibody may be detected directly but it is preferred to attach the probe to a protein (e.g., a secondary antibody) that specifically binds the primary antibody. Secondary antibody may be raised against the heavy or light chain constant region of the primary antibody. This procedure amplifies the signal generated by an antigen-antibody conjugate because each primary antibody will bind many secondary antibodies. Alternatively, amplification may occur through other specific interactions such as biotin-streptavidin. Antibody binding is performed in a small volume to reduce usage of expensive reagents and maintain a high binding rate; evaporation of this small volume is reduced by incubation in a humidity chamber. The signal generating moiety is preferably an enzyme which is not otherwise present in the tissue. For example, alkaline phosphatase and horseradish peroxidase may be attached to the secondary antibody or conjugated to streptavidin. Substrates are available for these enzymes that generate a chromogenic, fluorescent, or luminescent product that can be detected visually.

The staining pattern for antigen may be used to localize expression of the antigen in the context of cellular structures revealed by counterstaining. Antigen expression can identify cell or tissue type, developmental stage, tumor prognostic markers, degenerative metabolic processes, or infection by a pathogen.

Antigen-antibody binding may also be visualized with radioactive, fluorescence, or colloidal metal probes by autoradiography, epifluorescent microscopy, or electron microscopy respectively. Similar probes may be used to detect nucleic acid in the tissue section by in situ hybridization to identify genetic mutations or transcripts; alternatively, the nucleic acid (DNA or RNA) may be extracted from tissue sections and analyzed directly by blotting, or amplified prior to further genetic analysis.

Mutations may be germline and used to trace genetic predisposition of disease, or mutations may be somatic and used to determine genetic alterations in disease pathogenesis. The disease may be a metabolic or neurologic disorder, malignancy, developmental defect, or caused by an infectious agent. The present invention preserves material for genetic analysis by a simple procedure and room temperature storage.

Example 12

Pressure Assisted Tissue Histology (PATH)

It has also been discovered that tissue specimens can be processed more rapidly and reliably for histological examination by processing the specimen under elevated pressures. The elevated pressures greatly decrease the time required to perfuse the tissue with reagents used in the preparation of the tissue specimens for histological examination.

Histological tissue processing is widely used for the microscopic study of diseased tissue, which is an important tool in anatomic pathology. The histological process typically consists of the following steps: (a) fixation (tissue preservation), (b) processing (dehydration and clearing of tissue), (c) embedding (turning tissues into a hardened block suitable for sectioning by a microtome), (d) sectioning (the creation of 2-50 micron sections from the embedded tissue for mounting on a slide), and (e) staining (the use of dyes to provide contrast to the tissue being examined, including the use of biomolecule-specific dyes, antibodies, and biomolecule-specific probes). The PATH method described in this disclosure encompasses steps a-c of the histology process.

In the disclosed method of rapidly processing tissue for histological examination, the tissue is placed in a tissue fixative under elevated pressure for a sufficient period of time to increase the perfusion of the fixative into the tissue. The tissue is then dehydrated and cleared under high-pressure conditions, and embedding medium is perfused under high-pressure conditions into the tissue to harden it for examination. The high-pressure conditions can be maintained during the entire period during which fixation, dehydration, clearing and embedding occurs, or the pressure can be decreased between the processing steps. The elevated pressure at which each of the steps is carried out can differ or can be maintained uniform.

In a particular example, this pressure-assisted tissue histology (PATH) method includes:

(a) placing tissue (such as a tissue specimen) in a tissue fixative, for example in a vial;

(b) applying elevated pressure at a constant or variable temperature to the vial for a period of time sufficient to cause the complete perfusion of the fixative into the tissue;

(c) incubating the tissue for a sufficient time to allow for complete fixation of the tissue;

(d) replacing the fixative with a sequential series of solvents to dehydrate and clear the tissue;

(e) perfusing embedding medium into the tissue to harden the tissue;

(f) reducing the elevated pressure and temperature; and (g) recovering the tissue from the vial.

The recovered tissue is fixed and embedded in a medium suitable for storage, sectioning, and histological processing for examination for research or pathology. The tissue may undergo further histological processing, such as sectioning the fixed tissue into thin slices, for example with a microtome, for subsequent microscopic anatomical examination.

A variety of starting tissues can be subjected to high-pressure fixation, such as whole organs, organ sub-structures, surgical tissue biopsies, punch biopsies, fine-needle aspirate biopsies, bone, biological fluids, and snap-frozen tissues. The tissues may be placed in a vial for fixation, but the vial is ideally compatible with all the tissue processing solvents, and all said tissue processing pressure and temperatures. The vial may be bar-coded for identification and tracking of the vial and the tissue specimen that it contains.

A wide variety of fixative solutions may be used, such as formaldehyde, paraformaldehyde, glutaraldehyde, picric acid (Bouin's solution), mercurials (B-5 and Zenker's solution), oxidizing agents (potassium permanganate, osmium tetroxide), and 1-ethyl-3-(3-dimethylaminopropyl). Solvents useful for the tissue dehydration steps are not particularly limited, and include solvents such as methanol, absolute ethanol, aqueous ethanol solutions, acetone, dioxane, methyl salicylate, and HEMO-DE®. The tissue may be cleaned with solvents such as xylene, Clearite, HEMO-DE®, and cedar wood oil. Materials in which the fixed tissue may be embedded include paraffin, paraffin-containing compounds, araldite, celloidin, DURCUPAN™ embedding medium, epoxy, glycol methacrylate, hydroxypropyl methacrylate, JB-4™ embedding medium, Spurr, LR WHITE™ embedding medium, methyl methacrylate, glycol methacrylate, and epon.

The elevated pressure under which fixation occurs may be generated in any closed vessel having an air pumping system (an air or inert gas hydraulic process), or a high-pressure generator (a manually operated piston screw process). The pressure of the pumping systems or high-pressure generators can be increased using gas boosters or hydraulic intensifiers. Manufacturers of complete high-pressure systems and individual system components include Pressure Biosciences (South Easton, Mass.), High-Pressure Equipment Company (Erie, Pa.), and AppliTech Corporation (Lancaster, Pa.).

In certain embodiments, the instrument and process also maintain the tissue, fixative, dehydrating solvents, clearing solvents, and embedding material at a specific temperature (or specific temperatures) and pressures. Different temperatures may be necessary for each step of histological tissue processing. The temperature at which the elevated pressure process is carried out is not particularly limited, but is preferably between 0 and 120° C. Most preferably, the incubation temperature is greater than room temperature, for example between a minimum of 24° C. or 37° C. and a maximum of 80° C. or 100° C. (for example 24-80° C., 37-80° C., 24-100° C. and 37-100° C.). The elevated pressures at which the materials are maintained are those elevated pressures at which the PAMR method is performed. In particular examples, the elevated pressure is greater than 1000 psi, for example between 1,000 and 100,000 psi. More preferably, the elevated pressure is between 10,000 and 75,000 psi, for example between 10,000 and 40,000 psi or 45,000 psi, such as 43,000-45,000 psi. The elevated pressure and temperature may be applied for a sufficient period of time to achieve fixation of the tissue specimen, for example at least 15 minutes, or a period of time between 15 minutes and 5 hours, for example between 15 minutes and 3 hours, such as between 15 and 60 minutes.

In additional embodiments, the elevated pressure is applied for two or more cycles, where one cycle is a period of time at elevated pressure (for example, at least about 30 seconds, about 60 seconds, about 90 seconds, about 2 minutes or more) followed by a period of time at ambient pressure (such as at least about 15 seconds, about 20 seconds, about 25 seconds, about 30 seconds, about 40 seconds, about 50 seconds, about 60 seconds, or more). In some examples, the elevated pressure is applied for 2-100 cycles (such as 5-90 cycles, 10-75 cycles, or 20-60 cycles). In other examples, the elevated pressure is applied for at least 2 cycles, at least 5 cycles, at least 10 cycles, at least 20 cycles, at least 30 cycles, at lest 40 cycles, at least 50 cycles, at least 60 cycles, at least 70 cycles, at least 80 cycles, at least 90 cycles, at least 100 cycles, or more. The temperature at which the elevated pressure process is carried out is not particularly limited, but is preferably between 0 and 120° C. Most preferably, the incubation temperature is greater than room temperature, for example between a minimum of 24° C. or 37° C. and a maximum of 80° C. or 100° C. (for example 24-80° C., 37-80° C., 24-100° C. and 37-100° C.). The elevated pressures at which the materials are maintained are those elevated pressures at which the PAMR method is performed. In particular examples, the elevated pressure is greater than 1000 psi, for example between 1,000 and 100,000 psi. More preferably, the elevated pressure is between 10,000 and 75,000 psi, for example between 10,000 and 40,000 psi or 45,000 psi, such as 43,000-45,000 psi. In a particular example, the elevated pressure is applied for 60 cycles, where one cycle is 60 seconds at 10,000 psi followed by 25 seconds at ambient pressure.

The fixative, dehydrating solvents, clearing solvents, and embedding materials may be changed manually. For example, following each of the aforementioned tissue histology processing steps the pressure of the instrument is reduced to ambient pressure, the solvent currently in said vial is removed, and the next solvent in the tissue processing sequence is added to the vial. The pressure and temperature are then increased to values appropriate for the next tissue processing step. The elevated pressure and temperature of each such step may be maintained for at least 15 minutes, or a period of time between 15 minutes and 5 hours, for example between 15 minutes and 3 hours, such as between 15 and 60 minutes. Alternatively, the period of high pressure processing of all of the steps (not including the period of depressurization to change the solvent) may be at least 15 minutes, or a period of time between 15 minutes and 5 hours, for example between 15 minutes and 3 hours, such as between 15 and 60 minutes. Alternatively, changing between the fixative, dehydrating solvents, clearing solvents, and embedding material is accomplished automatically within the pressurized chamber (for example using pre-programmed robotics) without reducing the pressure of the vessel to gain access to it. Such automated processing can further reduce the total amount of time required for the high-pressure processing.

In some examples, the automated processor achieves automated sequential flushing and addition of tissue processing solvents accompanied by automated changes in processing temperature and time. The automated steps of solvent flushing, solvent addition, incubation temperature, and incubation time are controlled by the instrument with the use of a pre-programmed computer attached to the instrument. As a result of automated control, the entire histological tissue processing cycle (including embedding) is accomplished under automated control from start to finish without the need for user intervention.

In certain examples, the pressure instrument processes between 1 and 100 tissue vials (tissue specimens) simultaneously. Preferably, the pressure instrument can process between 5 and 25 tissue vials (tissue specimens) simultaneously. For example, the instrument contains holders for multiple vials, each of which contains the tissue specimens.

In some embodiments, the PAMR methods and PAAR methods are carried out in the same instrument in which PATH processing is performed.

Example 13

PATH of the Tissue Surrogate

Figure 17A:
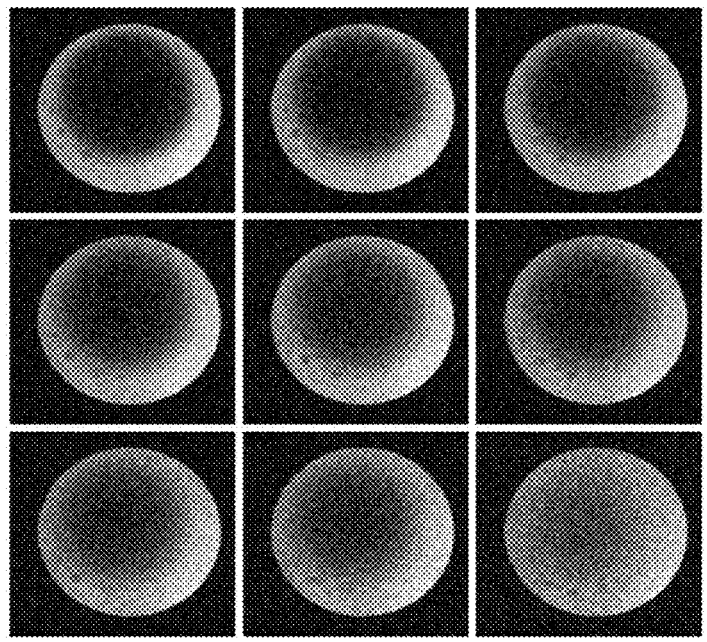
FIG. 17 illustrates pressure assisted tissue histology (PATH) of a lysozyme tissue surrogate. The lysozyme tissue surrogate (prepared as shown in FIG. 2) was cut into cylinders 10 mm long×3 mm wide. Half of the cylinders were placed in trifluoroethanol and allowed to incubate at 24° C. under ambient pressure for up to 110 min. The remaining cylinders were placed in the pressure apparatus and incubated at 24° C. at 30,000 psi pressure for up to 110 min. The control tissue cylinders and the pressure-treated tissue cylinders were then examined by magnetic resonance microscopy (Chesnick et al. *Bone* 40:904-912, 2007) using a 5 mm fluorine imaging coil. The resulting images are shown in FIG. 17A. The rate of solvent perfusion into the tissue surrogate was estimated by determining the percent of the cylinder surface exhibiting a fluorine NMR signal. Comparison of the control (squares) and pressure-treated (circles) tissue surrogates demonstrated an increase in the rate of solvent perfusion into the tissue surrogate at 30,000 psi pressure is shown in FIG. 17B.
Figure 17B:
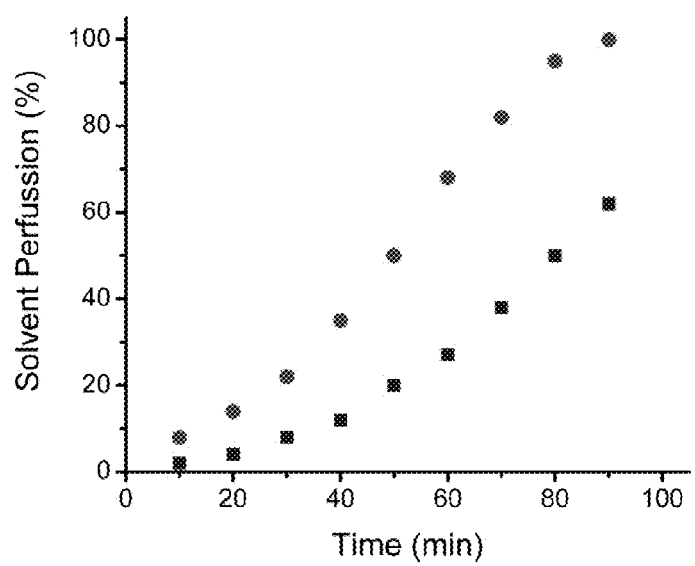

The increased rate of solvent perfusion into the lysozyme tissue surrogate under elevated pressure was determined. Lysozyme tissue surrogates (prepared as described above) were cut into cylinders 10 mm long×3 mm wide. Half of the cylinders were placed in trifluoroethanol and allowed to incubate at 24° C. under ambient pressure for up to 110 min. The remaining cylinders were placed in the pressure apparatus and incubated at 24° C. at 30,000 psi pressure for up to 110 minutes. The control tissue cylinders and the pressure-treated tissue cylinders were then examined by magnetic resonance microscopy (FIG. 17A) using a 5 mm fluorine imaging coil (Chesnick et al., *Bone* 40:904-912, 2007). The rate of solvent perfusion into the tissue surrogate was estimated by determining the percent of the cylinder surface exhibiting a fluorine NMR signal. Comparison of the control and pressure-treated tissue surrogates demonstrated an increase in the rate of solvent perfusion into the tissue surrogate at 30,000 psi pressure (FIG. 17B).

Example 14

PATH of a Muscle Tissue Punch

This example illustrates improved permeation of fixation agents into the tissue specimen at elevated pressures. Gel plugs were prepared by mixing equal volumes of a 4% agarose solution (SeaKem, Lonza, Switzerland) and 5% Knox® brand gelatin (Kraft Foods, Tarrytown, N.Y.) in deionized water and held at 65° C. The agar:gelatin mixture was dispensed into 300 µl polystyrene strip wells and allowed to set at 4° C. prior to fixation. Substantially cylindrical tissue punches having a 3 mm-diameter were extracted from the center of a 1 cm-thick section of pork tenderloin. The punches were seated into 1 cm long, 3 mm inner diameter (i.d.) thin-walled flat-bottomed glass tubes prior to fixation.

The gel plugs and tissue punches were incubated in 1 ml of 10% methanol-free formaldehyde (Polysciences, Inc., Warrington, Pa.) for 15, 30, or 60 minutes at ambient pressure or under elevated pressure. For the elevated pressure experiments, the tissue punches were placed into a FT-500 ND pulse tube (Pressure Biosciences, Inc., South Easton, Mass.) and incubated under isobaric pressure (35,000 psi) in a NEP 2320 BAROCYCLER® high pressure instrument (Pressure Biosciences). The gel plugs and tissue punches were immersed in FLUORINERT™ electronic liquid (FC-77, Oakwood, West Columbia, S.C.) prior to the magnetic resonance imaging (MRI) experiment. This fluorinated solvent contains no protons so it appears dark on all MRI images. The FC-77 does not penetrate the sample, effectively stopping the fixation process while preventing the sample from drying out during the MRI experiment. All MRI images were acquired on a BIOSPEC® spectrometer (Bruker Biospin Corp., Billerica, Mass.) coupled to a 7-Tesla horizontal bore magnet (300 MHz for protons).

Two-dimensional slice images, representing a 1-mm slice taken parallel to the long axis of the sample with an in-plane resolution of 195 microns, show the formaldehyde diffusion front. T2-maps, calculated on a pixel-by-pixel basis from 16 images acquired with a multi-echo sequence (TR/TE, 5000/10 ms), were scaled so that unfixed material with high T2 values appeared red to light green (light areas) and formalin-fixed material with low T2 values appeared dark blue to violet (dark areas) (Jones et al. *Biotechniques* 42: 569-570, 2007).

Figure 18:
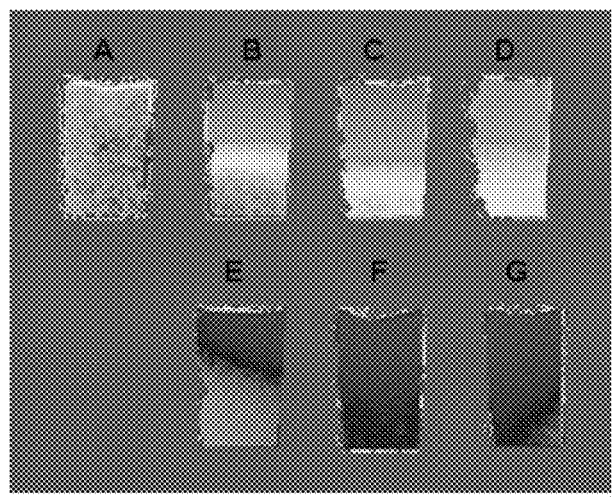
FIG. 18 is a series of digital T2 images obtained by magnetic resonance imaging (MRI) of agarose/gelatin plugs. (A) unfixed gel plug; fixed in 10% formaldehyde at atmospheric pressure for: (B) 15 min; (C) 30 min; and (D) 60 min. Fixed in 10% formaldehyde at 35,000 psi for: (E) 15 min; (F) 30 min; and (G) 60 min. All T2 maps were scaled so that unfixed material appeared lighter colored and fixed material appeared dark.

T2 maps of each time-pair of un-pressurized and pressure-treated gel plug are shown in FIG. 18 and were calculated from a total of 16 images. The unfixed gels (0 minute and portions of the non-pressure-treated gels) with high T2 values were scaled to appear red (lighter areas), while the completely fixed areas with low T2 values appear blue to violet (dark areas). As shown in FIG. 18A, the samples fixed according to standard histological protocols at atmospheric pressure had a very well-defined formaldehyde diffusion front and were incompletely fixed. After even 1 hour, there remained clearly demarcated fixed and partially fixed areas. Complete fixation at ambient pressure required multiple changes of formaldehyde over 4 hours. However, for the samples fixed under elevated pressure, the diffusion of formaldehyde throughout the gel was more uniform and complete after 15 to 30 minutes (FIG. 18 E-G).

Figure 19:
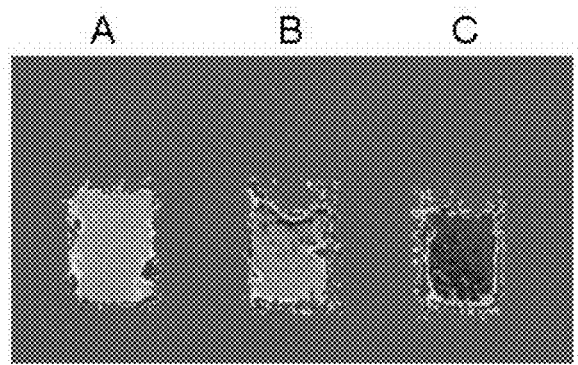
FIG. 19 is a series of digital T2 images obtained by MRI of 3 mm tissue punches from porcine muscle showing (A) non-formaldehyde-treated tissue; (B) tissue fixed in 10% formaldehyde for 30 minutes at ambient pressure; (C) tissue fixed in 10% formaldehyde for 30 minutes at elevated pressure (35,000 psi).

A similar effect was observed for the tissue punches. After incubation in formaldehyde at atmospheric pressure, the material appeared to be only partially fixed, as observed by MRI. When the tissue punches were fixed under elevated pressure, the formaldehyde appeared to have diffused more uniformly and completely throughout the sample as seen by comparing the T2 maps of the un-pressurized and pressure-treated samples as shown in FIG. 19. The isolated dark areas in the images represent free water collected around the periphery of the tissue punch.

Example 15

PATH with Pressure Pulses

Porcine kidney was grossed into 8 mm×8 mm×8 mm pieces and then incubated in 10% neutral buffered formalin for 24 hours at ambient pressure (14.7 psi), 1.5 hours at ambient pressure, or 60 cycles of elevated pressure, where 1 cycle consisted of 60 seconds at 10,000 psi, followed by a resting period of 25 seconds at ambient pressure. The fixed tissue was then dehydrated through a series of graded alcohols (70%, 85% and 100% ethanol for 30 min each), 2 changes of xylene (30 min each) and incubated in liquid paraffin (60° C., overnight) at ambient pressure before embedding. Sections (5 µm) were cut from the center of each paraffin block, and the sections were stained with hematoxylin and Eosin Y.

Figure 20:
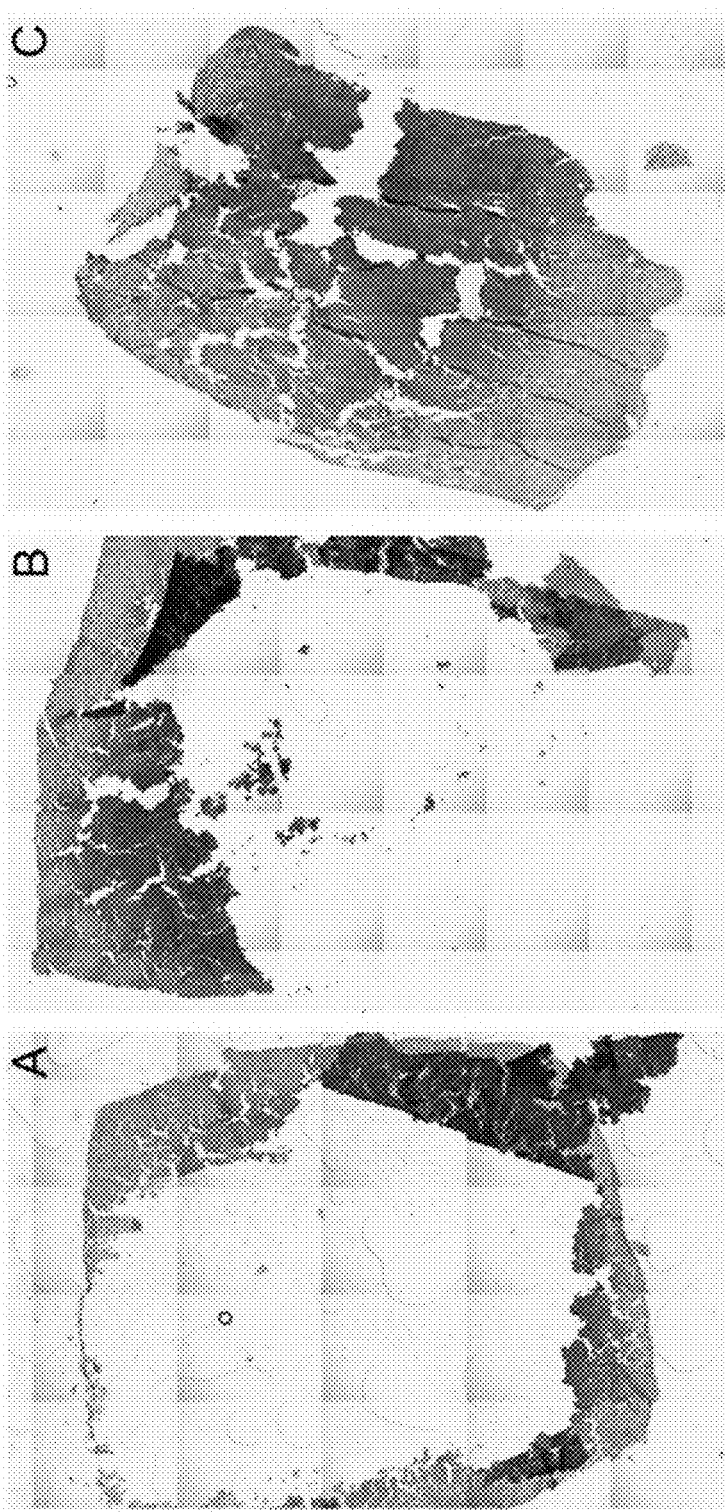
FIG. 20 is a series of digital images of hematoxylin and eosin stained sections of porcine kidney fixed in 10% neutral buffered formalin for (A) 24 hours at ambient pressure, (B) 1.5 hours at ambient pressure, or (C) 60 cycles of elevated pressure (each cycle was 60 seconds at 10,000 psi followed by 25 seconds at ambient pressure).

For tissue fixed at ambient pressure, the formaldehyde only penetrated through approximately the outermost 1 mm of the tissue, resulting in a thin ring of fixed tissue with an unfixed center that did not adhere well to the microscope slide, resulting in tissue loss (FIGS. 20A and B). Tissue which was fixed under cycles of pressure exhibited improved penetration of the fixative, as shown by the reduced tearing of the tissue (FIG. 20C).

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of processing tissue for histological examination, comprising:
    placing tissue in a tissue fixative under elevated pressure for a sufficient period of time to increase the perfusion of the fixative into the tissue, wherein the elevated pressure is at least 1000 psi;
    dehydrating the tissue by exposing it to a sequential series of dehydrating solvents under the elevated pressure; and
    perfusing embedding medium into the tissue under the elevated pressure to harden the tissue.

2. The method of claim 1, wherein placing tissue in a tissue fixative under elevated pressure for a sufficient period of time to increase the perfusion of the fixative into the tissue comprises:
    (a) placing the tissue in the tissue fixative within a container;
    (b) applying the elevated pressure at a constant or variable temperature to the fixative in the container for a period of time sufficient to substantially completely perfuse the fixative into the tissue;

(c) incubating the tissue for a sufficient time at the elevated pressure to allow for fixation of the tissue;
(d) replacing the fixative with a sequential series of dehydration solvents to dehydrate and clear the tissue under the elevated pressure;
(e) perfusing embedding medium into the tissue under the elevated pressure to harden the tissue;
(f) reducing the elevated pressure; and
(g) recovering the tissue from the container, wherein the tissue is fixed and embedded in a medium suitable for storage, sectioning, and histological examination for research or pathology.

3. The method of claim 2, further comprising sectioning the recovered tissue into slices with a microtome for subsequent examination of microscopic anatomy.

4. The method of claim 3, further comprising exposing the tissue to a contrast agent selected from the group of biomolecule-specific dyes, antibodies, and biomolecule-specific probes.

5. The method of claim 2 wherein the container comprises a closed vessel comprising a pumping system or a high-pressure generator.

6. The method of claim 5, wherein the container further comprises a temperature controller that maintains contents of the container at a desired temperature.

7. The method of claim 6, wherein the temperature is between 24 and 100° C.

8. The method of claim 2, wherein the elevated pressure is between 1000 and 100,000 psi.

9. The method of claim 8, wherein the elevated pressure is between 10,000 and 45,000 psi.

10. The method of claim 2, wherein the elevated pressure of step (b) is applied for two or more pulses.

11. The method of claim 10, wherein each pulse comprises a period of time at elevated pressure and a period of time at ambient pressure.

12. The method of claim 2, wherein the elevated pressure and temperature of step (b) are maintained for between 15 minutes and 5 hours.

13. The method of claim 2, where the fixative, dehydrating agent, clearing agent, and embedding agent are changed automatically without pressure reduction or the need for user intervention.

14. The method of claim 1, wherein the tissue fixative comprises one or more of formaldehyde, paraformaldehyde, glutaraldehyde, picric acid, mercurials, osmium tetroxide, potassium permanganate, and 1-ethyl-3-(3-dimethylaminopropyl).

15. The method of claim 1, wherein the dehydrating solvents comprise one or more of methanol, ethanol, acetone, dioxane, methyl salicylate, and xylene.

16. The method of claim 1, wherein the embedding medium comprises one or more of paraffin, araldite, celloidin, epoxy, glycol methacrylate, hydroxypropyl methacrylate, Spurr, methyl methacrylate, glycol methacrylate, and epon.

* * * * *